United States Patent [19]

Norton et al.

[11] Patent Number: 5,486,701
[45] Date of Patent: Jan. 23, 1996

[54] METHOD AND APPARATUS FOR MEASURING REFLECTANCE IN TWO WAVELENGTH BANDS TO ENABLE DETERMINATION OF THIN FILM THICKNESS

[75] Inventors: Adam E. Norton, Palo Alto; Hung V. Pham, San Jose, both of Calif.

[73] Assignee: Prometrix Corporation, Santa Clara, Calif.

[21] Appl. No.: 218,975

[22] Filed: Mar. 28, 1994

Related U.S. Application Data

[63] Continuation-in-part of Ser. No. 899,666, Jun. 16, 1992, abandoned.

[51] Int. Cl.$^6$ ................................................. G01N 21/27
[52] U.S. Cl. ........................... 250/372; 356/381; 356/382
[58] Field of Search ........................... 250/372; 356/382, 356/381

[56] References Cited

U.S. PATENT DOCUMENTS

| | | | |
|---|---|---|---|
| 3,214,596 | 10/1965 | Schwerdt, Jr. et al. | 250/259 |
| 3,752,559 | 8/1973 | Fletcher et al. | 350/55 |
| 3,975,084 | 8/1976 | Block | 356/103 |
| 3,999,855 | 12/1976 | Hirschfeld | 356/103 |
| 4,106,856 | 8/1978 | Babish | 350/199 |
| 4,645,349 | 2/1987 | Tabata | 356/382 |
| 4,656,358 | 4/1987 | Divens et al. | 250/372 |
| 4,712,912 | 12/1987 | Messerschmidt | 356/73 |
| 4,758,088 | 7/1988 | Doyle | 356/346 |
| 4,795,256 | 1/1989 | Krause et al. | 356/320 |
| 4,844,617 | 7/1989 | Kelderman et al. | 356/372 |
| 4,899,055 | 2/1990 | Adams | 250/372 |
| 4,906,844 | 3/1990 | Hall | 250/225 |
| 4,945,220 | 7/1990 | Mallory et al. | 250/201.3 |
| 4,983,823 | 1/1991 | Isobe | 250/225 |
| 5,045,704 | 9/1991 | Coates | 250/372 |
| 5,067,805 | 11/1991 | Corle et al. | 359/235 |
| 5,146,097 | 9/1992 | Fujiwara et al. | 250/372 |
| 5,241,366 | 8/1993 | Bevis et al. | 356/381 |

FOREIGN PATENT DOCUMENTS

| | | | |
|---|---|---|---|
| 57-106846 | 7/1982 | Japan | 356/326 |
| 1-308930 | 12/1989 | Japan | 356/328 |

*Primary Examiner*—Constantine Hannaher
*Attorney, Agent, or Firm*—Limbach & Limbach

[57] ABSTRACT

A method and system for performing reflectance measurements of a sample using radiation having UV frequency components (preferably in a broad UV band) and visible frequency components (preferably in a broad band). Preferably, two detectors simultaneously receive a sample beam reflected from the sample surface. One detector generates a signal indicative of the sample beam components in the UV band and the other detector generates a signal indicative of the sample beam components in the visible band. By processing these two signals, the invention enables accurate measurement of the thickness of a very thin film on the sample. Preferably, the system determines a single effective wavelength for the UV radiation incident on the first detector and a single effective wavelength for the visible radiation incident on the second detector. Embodiments of the system can also measure reflectance spectra and refractive indices, and can determine lithographic exposure times. Preferred embodiments include an objective lens assembly having a pupil stop with an entrance portion with one or more relatively large apertures therethrough and an exit portion with one or more relatively small apertures therethrough. Illuminating radiation passes through the relatively large apertures before reflecting from the sample, and then passes through the relatively small apertures after reflecting from the sample. This design and pupil stop orientation dramatically increases the insensitivity of the system to ripple on the sample surface.

42 Claims, 5 Drawing Sheets

METHOD AND APPARATUS FOR MEASURING REFLECTANCE IN TWO WAVELENGTH BANDS TO ENABLE DETERMINATION OF THIN FILM THICKNESS

CROSS-REFERENCE TO RELATED APPLICATION

The present application is a continuation-in-part of U.S. patent application Ser. No. 07/899,666, filed Jun. 16, 1992, abandoned, entitled "Broadband Small Spot Spectral Reflectometer with Autofocus."

FIELD OF THE INVENTION

The invention relates to a method and apparatus for obtaining reflectance measurements of a sample under a microscope in two wavelength ranges (preferably the UV and visible ranges), and optionally also determining thickness of a very thin film on the sample from such measurements. The sample can be a semiconductor wafer including one or more thin (or very thin) layers over a silicon substrate.

BACKGROUND OF THE INVENTION

Reflectance data has a variety of uses. The thickness of the various coatings (either single layer or multiple layer) on the wafer can be determined from a reflectance or relative reflectance spectrum. Also, the reflectance at a single wavelength can be extracted. This is useful where the reflectance of photoresist coated wafers at the wavelength of lithographic exposure tools must be found to determine proper exposure levels for the wafers, or to optimize the thickness of the resist to minimize reflectance of the entire coating stack. The refractive index of the coating can also be determined by analysis of an accurately measured reflectance spectrum.

It is especially useful, for a variety of industrial applications, to measure the thickness of a very thin film (less than about 300 angstroms in thickness) on a sample, by reflectance measurements of the sample under a microscope. For example, the sample can be a semiconductor wafer, and the very thin film can be coated on a silicon substrate of the wafer.

Because of the tight tolerance requirements typically required in the semiconductor arts, an accurate means for obtaining reflectance measurements of a wafer is needed. In conventional reflectance measurement systems, monochromatic or broadband radiation is reflected from the wafer, and the reflected radiation is collected and measured.

FIG. 1 is a broadband small spot spectral reflectometer, camera, and autofocus apparatus, over which the present invention represents an improvement. The FIG. 1 system includes an optical system for measuring reflectance of a sample 3 (which is typically a wafer), and means for focusing sample 3 with respect to the optical system, including an illumination subsystem, a reflectometer subsystem, a viewing subsystem, and an autofocus subsystem, wherein any given optical element may be part of more than one subsystem.

The illumination subsystem includes lamp 10 (typically a xenon arc lamp) which emits radiation beam 12 (comprising visible and/or UV radiation), lamp housing window 14, off-axis paraboloid mirror 16, flip-in UV cutoff filter 18, color filter wheel 20, a flat mirror 22, a concave mirror 24, aperture mirror 28 with flip-in forty-micron fine focus aperture 30, large achromat 32, field illumination shutter 31, fold mirror 36, and small achromat 38.

The illumination system provides combined beam 42 comprising measurement beam 25 and field illumination beam 34. Lamp 10 emits beam 12 through lamp housing window 14. Window 14 is provided to contain lamp 10 should the lamp crack and explode. Although window 14 is not necessary for optical reasons, it can function (with lamp heatsink window 14a, and with baffles not shown in FIG. 1) to keep lamp cooling air from being drawn through the optical path (since such flowing air could otherwise cause shimmering of the arc image and contribute to noise). A xenon lamp is preferred over other lamps such as tungsten or deuterium lamps, because a xenon lamp will give a flatter output covering a spectrum from UV to near infrared. Alternatively, a tungsten lamp and a deuterium lamp can be used in combination to cover the same spectrum covered by a xenon lamp, but this combination still leaves a gap in brightness in the mid-UV wavelengths. Brightness of the spectrum is important, because with less intensity, reflected radiation must be collected for longer periods, thus lower intensities slow the measurement process.

Off-axis paraboloid mirror 16 collimates beam 12, which can be optionally filtered by flip-in UV cutoff filter 18 and color filter wheel 20. Flip-in UV cutoff filter 18 is used in part to limit the spectrum of beam 12, so that when beam 12 is dispersed by a diffraction grating, the first and second order diffraction beams do not overlap. Part of beam 12 is reflected by flat mirror 22 onto concave mirror 24 to form measurement beam 25. Optionally, concave mirror 24 can focus beam 25 onto the end of a large-core silica fiber which acts as a radial uniformer (in an effort to attain a radially symmetric beam cross-section at the output of the large-core silica fiber regardless of the intensity pattern in a cross section of measurement beam 25 at the input of the large-core silica fiber). Without such a radial uniformer, it is possible that the arc in lamp 10 might shift and cause the intensity of light across a cross section of measurement beam 25 to shift causing apparent fluctuations in the relative reflectance spectrum determined from the output of photodiode arrays 72 and 74. However, in many applications it is preferable to omit the large-core fiber. Without the large-core fiber, mirror 24 focuses an image of the arc onto aperture mirror 28. The radiation emanating from each point on the image of the arc expands in a uniform cone, typically producing a uniform circle of illumination at beam divider 45.

Another part of beam 12, field illumination beam 34, is focused by large achromat 32 near fold mirror 36, causing fold mirror 36 to reflect an image of lamp 10 toward small achromat 38. Small achromat 38 collects the radiation in beam 34 before it reflects from aperture mirror 28. Aperture mirror 28 is preferably a fused silica plate with a reflective coating on one side, with a 150 micron square etched from the reflective coating to provide an aperture for beam 25. The aperture is placed at one conjugate of objective 40. The field illumination can be turned off by placing field illumination shutter 31 in the optical path of field illumination beam 34.

Narrow measurement beam 25 and wide field illumination beam 34 are rejoined at aperture mirror 28, with field illumination beam 34 reflecting off the front of aperture mirror 28, and measurement beam 25 passing through the aperture. The use of flip-in fine focus aperture 30 is explained below. The reflectometer, viewing, and autofocus subsystems of the FIG. 1 system include objective 40, beamsplitter mirror 45, sample beam 46, reference beam 48, concave mirror 50, flat mirror 43, reference plate 52 with a reference spectrometer pinhole therethrough, sample plate 54 with a sample spectrometer pinhole therethrough, second fold mirror 68, diffraction grating 70, sample linear photodiode array 72, reference linear photodiode array 74, reference photodiode 95, sample photodiode 93, an achromat with a short focal length and a right angle prism (not shown), beamsplitter cube 84, penta prism 86, achromats 88 and 90 with long focal lengths, third fold mirror 89, focus detector 98, neutral density filter wheel 97, fourth fold mirror 91, and video camera 96.

Objective 40, which can be a reflective objective (as shown in FIG. 1) or a transmissive objective (as shown in FIGS. 3–6), preferably has several selectable magnifications. In one embodiment, objective 40 includes a 15× Schwarzchild design all-reflective objective, a 4× Nikon CFN Plan Apochromat (color corrected at three wavelengths), and a 1× UV transmissive objective, all mounted on a rotatable turret which allows for one of the three objectives to be placed in the optical path of sample beam 46.

The measurement of the relative reflectance spectrum of wafer 3 will now be described. When field illumination shutter 31 is placed in the path of field illumination beam 34, combined beam 42 comprises only measurement beam 25. Combined beam 42 is split by beamsplitter mirror 45, a totally reflecting mirror placed so as to deflect half of combined beam 42 towards objective 40, thus forming sample beam 46, the undeflected half of combined beam 42 forming reference beam 48. Importantly, because sample beam 46 and reference beam 48 are derived from the same source (lamp 10) and because combined beam 42 is radially uniform, reference beam 48 and sample beam 46 have proportionally dependent spectral intensities. Furthermore, since beamsplitter mirror 45 is a totally reflecting mirror in half of an optical path rather than a partially reflecting mirror in the entire optical path, a continuous broadband spectrum is reflected with good brightness.

Reference beam 48 does not initially interact with beamsplitter mirror 45, but instead illuminates concave mirror 50. Concave mirror 50 is slightly off-axis, so reference beam 48 is reflected onto the reverse face of beamsplitter mirror 45, and flat mirror 43 re-reflects reference beam 48 into alignment with the reference spectrometer pinhole through plate 52. Flat mirror 43 is provided to realign reference beam 48 with sample beam 46 so that both beams pass through their respective spectrometer pinholes substantially parallel.

The focal length of concave mirror 50 is such that reference beam 48 is in focus at the reference spectrometer pinhole (which extends through plate 52). The radiation passing through the reference spectrometer pinhole and reflecting from fold mirror 68 is dispersed by diffraction grating 70. The resulting first order diffraction beam is collected by reference linear photodiode array 74, thereby measuring a reference relectance spectrum.

Sample beam 46 is reflected from beamsplitter mirror 45 towards objective 40, which focuses sample beam 46 onto wafer 3, and the reflected sample beam 46 is focused by objective 40 onto the sample spectrometer pinhole (which extends through plate 54). The reflected sample beam 46 does not interact with beamsplitter mirror 45 on the reflected path, because sample beam 46 passed through the space behind beamsplitter mirror 45, through which reference beam 48 also passes. The radiation passing through the sample spectrometer pinhole and reflecting from fold mirror 68 is dispersed by diffraction grating 70. As with the reference beam, the resulting first order diffraction beam of the sample beam is collected by sample linear photodiode array 72, thereby measuring the sample spectrum.

The relative reflectance spectrum can be simply obtained by processing the outputs of arrays 72 and 74 in processor 100, by dividing the sample light intensity at each wavelength (the output of array 72) by the reference intensity at each wavelength (the output of array 74). Typically, this involves 512 division computations, in cases in which each of arrays 72 and 74 is a 512-diode linear photodiode array. A typical relative reflectance spectrum will include components ranging from 220 nm to 830 nm.

In some embodiments, diffraction grating 70 is a concave holographic grating and the spectrometer pinholes (through plates 52 and 54) are 15 mm apart. This embodiment of diffraction grating 70 is holographically corrected to image multiple spectra, since the 15 mm spacing does not allow for both beams to be centered on the grating. One such grating is a multiple spectra imaging grating supplied by Instruments S.A. It is also desirable that grating 70 be designed so that the angle of detectors 72 and 74 causes reflections from the detectors to propagate away from the grating.

The FIG. 1 system includes an autofocus subsystem having a coarse-focus mode to allow for wide range lock-in, and a fine-focus mode for use once a coarse focus is achieved. In the coarse-focus mode, flip-in fine-focus aperture 30 is flipped out of the optical path, and the square aperture of aperture mirror 28 is imaged onto detector 98. Variations on the FIG. 1 system may not implement the coarse-focus mode.

Detector 98 has a position output, which is dependent on the position of the centroid of the radiation falling on detector 98, and an intensity output, which is dependent on the incident intensity at detector 98. Detector 98 is also positioned to avoid dark regions of the out-of-focus image. In the coarse-focus mode, the centroid of the image falling on detector 98 indicates not only the direction in which focus lies, but also how far out of focus wafer 3 is. The Z position of wafer 3 (the separation between wafer 3 and objective 40) is then adjusted until the centroid of the light falling on detector 98 is centered near the center of detector 98. With the appropriate positioning and feedback mechanism, wafer 3 can be kept in coarse focus while the wafer is being moved in the X and Y directions. In one embodiment, a feedback loop between detector 98 and a servo motor which adjusts the focus is disabled when no light falls on detector 98. This is to prevent uncontrolled movement of the stage supporting wafer 3.

For fine focus, flip-in aperture 30 is flipped into the optical path of measurement beam 25, resulting in a smaller square image reaching detector 98. The smaller square image has a size of about 40 microns with a IX objective. Since flip-in aperture 30 is the same size as the aperture though plate 54, and since the two apertures are at conjugates of objective 40, when wafer 3 is in focus, very little radiation strikes plate 54 (away from the aperture through plate 54) to be reflected onto detector 98. Thus, in the fine-focus mode, the intensity output of detector 98 is used to bring wafer 3 into focus, with the Z position of wafer 3 being adjusted until the intensity output of detector 98 is minimized.

In an operating mode for measuring the thickness of very thin film 3a (VTF 3a) on sample 3, the FIG. 1 system employs sample VTF photodiode 93 and reference VTF photodiode 95. Dichroic mirror 152 mounted on a moveable arm flips into the beam path immediately beyond apertured plates 52 and 54. The dichroic mirror reflects UV radiation (with wavelength between 400 nm and 280 nm) and transmits visible light. The reflected UV from the reference beam is focused by fused silica lens 155, reflected by fixed dichroic mirror 156, and finally falls on UV enhanced silicon photodiode 95 (the "reference VTF photodiode"), and the reflected UV from the sample beam is focused by fused silica lens 153, reflected by fixed dichroic mirror 156, and finally falls on UV enhanced silicon photodiode 93 (the "sample VTF photodiode"). Second dichroic mirror 156 is needed to filter out residual visible light. The radiation transmitted through first dichroic 152 continues through the normal spectrometer path.

Each of photodiodes 93 and 95 measures a single intensity value, but typically this value is an average over a broadband frequency range of interest (in the UV range) so that the two photodiodes provide sufficient information for calculating a relative reflectance (or reflectance) value representing an average over such broadband frequency range. Photodiodes 93 and 95 are preferably selected to have sensitivity to a broad range of wavelengths in the UV band, with both photodiodes having substantially similar peak sensitivity wavelengths. When the response of sample photodiode 93 is divided by the response of reference photodiode 95, the result is a value indicative of the relative reflectance of wafer 3 over wavelengths in the UV band, with the peak sensitivity wavelength having more weight in the measure of relative reflectance than other wavelengths. The measured relative reflectance value can be calibrated to generate a signal indicative of the true reflectance of the sample in the UV band.

The reasons for employing photodiodes 93 and 95 to measure the thickness of a very thin film (VTF) on wafer 3 are as follows.

When a relatively thick film (having optical thickness greater than ¼ the wavelength of the illuminating radiation) is deposited on a reflective substrate, the interference between light reflecting from the top and bottom interfaces creates maxima and minima in the reflectance spectrum. The thickness can be determined by finding the wavelength position of the extrema, or by finding the best match between the shape of the measured spectrum and the shape of theoretically calculated spectra of different thicknesses.

As the film becomes thinner, the number of extrema are reduced. With films so thin that the last minimum has disappeared, there is a thickness range of a couple of hundred angstroms in which the curvature of the spectrum still provides important information about the film thickness, but the absolute intensity of the spectrum becomes increasingly more important as the film becomes thinner. Very thin films (films having optical thickness much less than ¼ the illuminating wavelength) have reflectance spectra that are just a few percent dimmer than the reflectance spectrum of a bare substrate. Thus, when measuring thick films, errors in the wavelength scale of the spectrum are more significant, whereas with very thin films the vertical scale (absolute intensity of measured reflectance) should be measured accurately.

The radiation incident on photodiodes 93 and 95 has propagated through an optical path that bypasses grating 70 to avoid the "grating tilt effect," and each of photodiodes 93 and 95 preferably receives a broad range of UV wavelengths. The grating tilt effect is that a change in orientation (tilt) of wafer 3 will cause radiation falling on grating 70 to shift using a slightly different portion of the surface of grating 70. Typical concave gratings used to implement grating 70 have sharply varying efficiencies across their surfaces, and so a change in sample tilt causes an undesirable change in the signal diffracted by grating 70.

The UV radiation incident on photodiodes 93 and 95 is preferably not filtered through a narrow band filter (because if it were, too little radiation would reach the photodiodes). To avoid the need to apply a complicated algorithm (assuming a weighted average of many incident wavelengths) to compute film thickness, processor 100 of the FIG. 1 system determines a single effective wavelength for the broadband UV incident on each of photodiodes 93 and 95. The analog output of photodiodes 93 and 95 is digitized (and otherwise processed) in electronic circuitry 90 before undergoing digital processing in processor 100.

Although measurements made using photodiode 93 alone may be sufficient to measure film thickness in some contexts, additional measurements are usually made using photodiode 95 in the reference beam path, to correct for lamp noise.

The processing steps performed on the output of photodiodes 93 and 95 are described in detail below. These processing steps are briefly summarized in this paragraph. Before each sample 3 is measured, darknoise is measured for each of photodiodes 93 and 95. Darknoise for the sample channel is the DC offset occuring with no sample present on the sample stage (representing stray light and cross talk from the reference path, which is to be subtracted from sample measurements), and darknoise for the reference channel is the DC offset occuring with an opaque disk in the optical path at the location of color filter 20 (e.g., an opaque disk of a color filter wheel implementation of color filter 20). Darknoise is subtracted from the output signal of each of photodiodes 93 and 95, and the sample channel signal (the corrected output of photodiode 93) is then divided by the reference channel signal (the corrected output of photodiode 95) to yield a reading that is proportional to sample reflectance but largely independent of lamp intensity fluctuations.

As noted, photodiodes 93 and 95 are preferably sensitive to a range of UV wavelengths, with photodiode 95 receiving reference UV radiation and photodiode 93 receiving UV radiation that has reflected from the sample. There are two advantages to measuring very thin films with UV radiation rather than visible radiation. The first is that, since the wavelength range of UV radiation is shorter than that of visible light, the optical thickness of the measured film expressed in units of wavelengths is actually greater. The second advantage applies mainly to measurements of films on silicon substrates. There is a sharp change in the complex refractive index of silicon that occurs near 400 nm. If reflectance versus thickness is plotted for silicon dioxide on a silicon substrate (the most common VTF) for a single visible wavelength, the curve is flat (zero derivative) at zero thickness, but drops and becomes increasingly steeper for greater thicknesses. The same curve (for UV radiation) has a non-zero derivative (slope) at zero thickness. Thus, sensitivity to changes in the thickness of this type of VTF near zero film thickness does not drop nearly as quickly in the UV as it does in the visible.

Although the design of the FIG. 1 system substantially reduces many sources of error, since it includes means for automatically keeping the sample in focus and since its optics are designed to reduce sensitivity to sample tilt and variation in the illuminating radiation's intensity and spectrum, several difficulties arise when operating the FIG. 1 system to perform VTF measurements (using photodiodes 93 and 95).

Although the FIG. 1 system uses UV radiation to measure very thin film thickness, it must measure the absolute reflectance to better than 0.05% to obtain the precision and stability required in many applications.

Although the FIG. 1 system can measure thickness of a 30 Angstrom (30 A) film on a substrate with a precision of less than 0.40 A (one sigma), and a stability less than 1.40 A (one sigma), this degree of precision and stability is inadequate for some applications. One contribution to instability is drift between a wafer sample and reference path during measurement. By measuring a reference sample (through the sample channel; not the reference channel) just before measuring the wafer (or other sample) of interest, it is possible to correct for any drift that had previously occurred, but if the test requires many sites to be measured (or if the room temperature varies quickly) the drift between measurements on the first and last sites on the wafer can be significant.

A second effect contributes even more to measurement error. The surface of a thin coating on a sample typically has nonuniform distance from objective 40, so that such distance varies from point to point on the sample surface. Typically, this is due to variation in the thickness of the sample substrate, with a uniformly thick coating following the substrate contours. Variation ("micro-ripple") in the position of the upper and lower surface of the coating (relative to objective 40) over a small area of the sample can act as a small lens to defocus radiation as the radiation reflects from the sample.

A third source of error is that the effect of two hertz lamp noise sometimes cannot be reduced to an acceptable level. Lamp noise can be exacerbated by many things, such as alignment, air currents, and the like, but the basic problem is that the reference path collects radiation from the illuminator at a different angle than the sample path.

A fourth source of error is that a high power (e.g., 15×) objective lens can be so sensitive to focus errors that the described auto-focus subsystem cannot effectively correct such errors.

Examples of other conventional film thickness measurement systems include those described in U.S. Pat. No. 5,241,366 issued Aug. 31, 1993 to Bevis et al., and U.S. Pat. No. 4,645,349, issued Feb. 24, 1987 to Tabata. The Tabata system determines thickness of a film from a measured reflectance spectrum. A broadband radiation source (16) illuminates a monochromator (19), which, through a partially reflecting mirror (22), illuminates a film (31). The monochromator filters the broadband radiation by reflecting it off a diffraction grating (20), and the monochromator output wavelength is selected by rotating the diffraction grating with respect to a directional mirror. A reflected beam from the film is reflected back along the original optical path, and is reflected out of the original optical path by the partially reflecting mirror. The reflected beam then illuminates a photo-multiplier tube (26), and the output of the photo-multiplier tube is connected to a graphics device (30), which is also connected to a wavelength output of the monochromator, allowing the graphics device to display a graph of reflectance versus wavelength. However, since a scanning monochromator is used, obtaining the reflectance spectrum is time consuming, and no means is provided to ensure that the intensity of the incident radiation is uniform over the time period of measurement. Furthermore, the system of Tabata assumes the sample is in focus. If the sample is not in focus, the reflected radiation may not be sufficiently focused by the objective to provide a useful spectrum. The optics also present special problems, because the diffraction grating must be precisely aligned with the directional mirror. The partially reflecting mirror is also difficult to manufacture with good efficiency when a very wide range of wavelengths are to be used. Even in the best case, the losses due to the partially reflecting mirror are squared, as the radiation must pass through the element twice.

SUMMARY OF THE INVENTION

Aspects of the method and apparatus of the present invention eliminate or substantially reduce the above-described limitations of the FIG. 1 system. In accordance with the invention, reflectance measurements of a sample are performed using illuminating radiation having frequency components in two wavelength bands (preferably both frequency components in a broad band in the UV range and frequency components in a broad band in the visible range). Preferably, two detectors simultaneously receive a sample beam reflected from the sample surface. One detector generates a signal indicative of the sample beam components in the UV band and the other detector generates a signal indicative of the sample beam components in the visible band. By processing these two signals, the invention enables accurate measurement of the thickness of a very thin film on the sample. In preferred embodiments, the system determines a single effective wavelength for the UV radiation incident on the first detector and a single effective wavelength for the visible radiation incident on the second detector.

In some embodiments, the system includes two reference channel detectors (in addition to the two sample channel detectors), and the illuminating radiation is split into a sample beam and a reference beam. The sample beam reflects from the surface of a sample and is directed to the two sample channel detectors (as described above). The reference beam does not reflect from the sample, but is directed to the two reference channel detectors. One reference detector generates a signal indicative of reference beam components in the UV band. The other reference detector generates a signal indicative of reference beam components in the visible band. By processing these two signals, as well as the two signals from the sample channel detectors, the thickness of a very thin film on the sample can be even more accurately determined.

By separately detecting both UV and visible radiation from the sample instead of radiation from a sample path and a reference path, the invention can determine a ratio of UV relectance to visible reflectance (both in a sample channel), which is largely independent of both micro ripple effects and lamp fluctuations. Measuring the ratio of reflectance at two known wavelengths (e.g., a single "effective" UV wavelength and a single "effective" visible wavelength) is as useful as measuring absolute reflectance for determining thickness.

Some embodiments of the inventive system also include a diffraction grating (e.g., grating 70), and reference channel and sample channel photodiode arrays (e.g., arrays 72 and 74).

In preferred embodiments, the objective lens system includes a pupil stop having an entrance portion with one or more relatively large apertures therethrough, and an exit portion with one or more relatively small apertures therethrough. Illuminating radiation passes through the relatively large apertures before reflecting from the sample, and then passes through the relatively small apertures after reflecting from the sample. This design and orientation of the pupil stop dramatically increases the insensitivity of the inventive system to ripple of the sample surface (e.g., micro-ripple in the position of the upper and lower surfaces of a uniformly-thick thin film coating on the sample), which dramatically improves the system performance, eliminates the need for optimizing the focus position for best ripple insensitivity, and reduces sensitivity of the system to sample tilt.

The invention has many applications, such as measuring refractive indices, measuring film thicknesses, and determining lithographic exposure times, and (in embodiments including a diffraction grating, and reference channel and sample channel photodiode arrays) measuring reflectance spectra.

DESCRIPTION OF THE PREFERRED EMBODIMENTS

Figure 1:
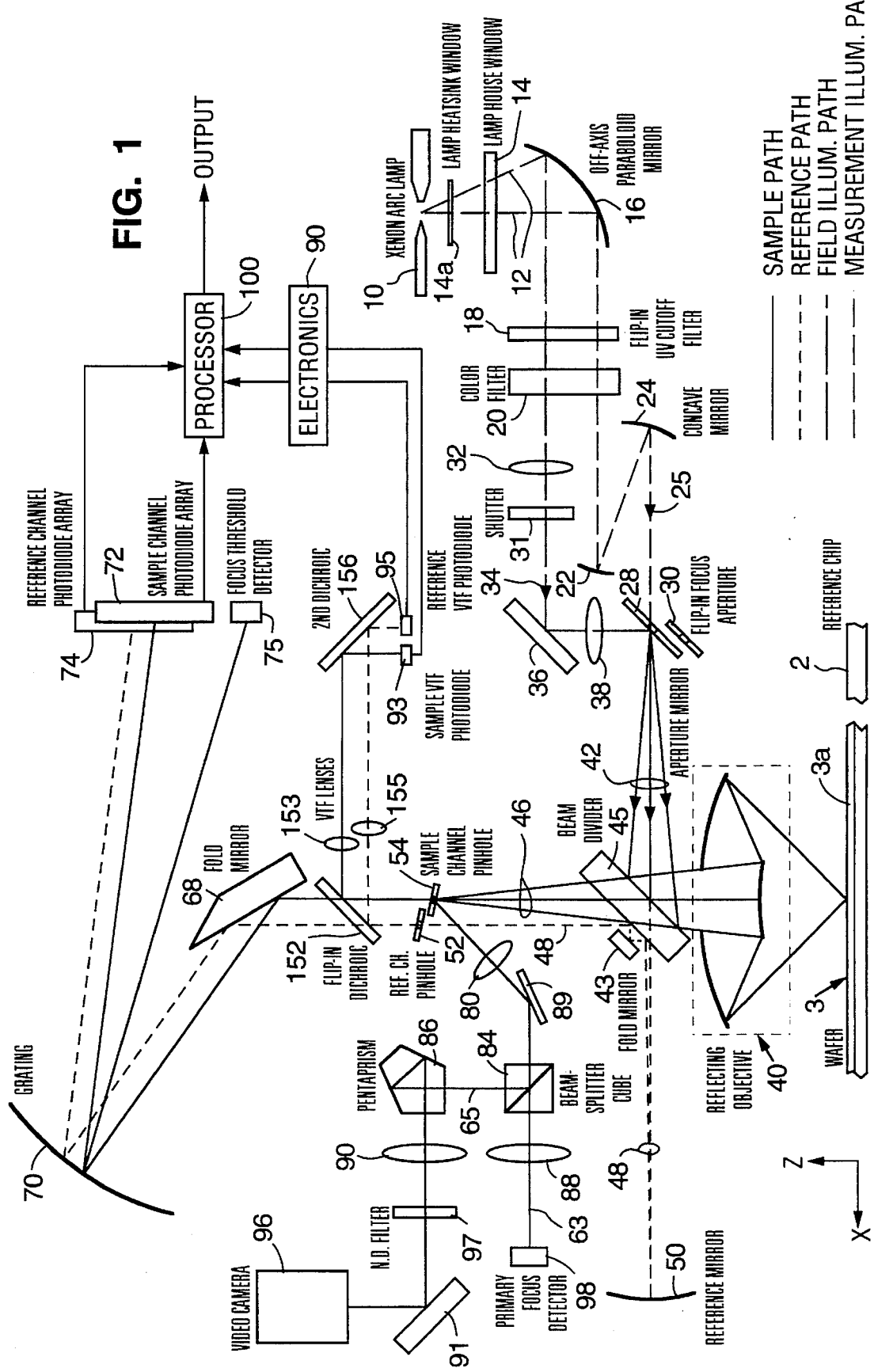
FIG. 1 is a schematic diagram of a broadband small spot spectral reflectometer, camera, and autofocus system (over which several aspects of the present invention represents an improvement).
Figure 2:
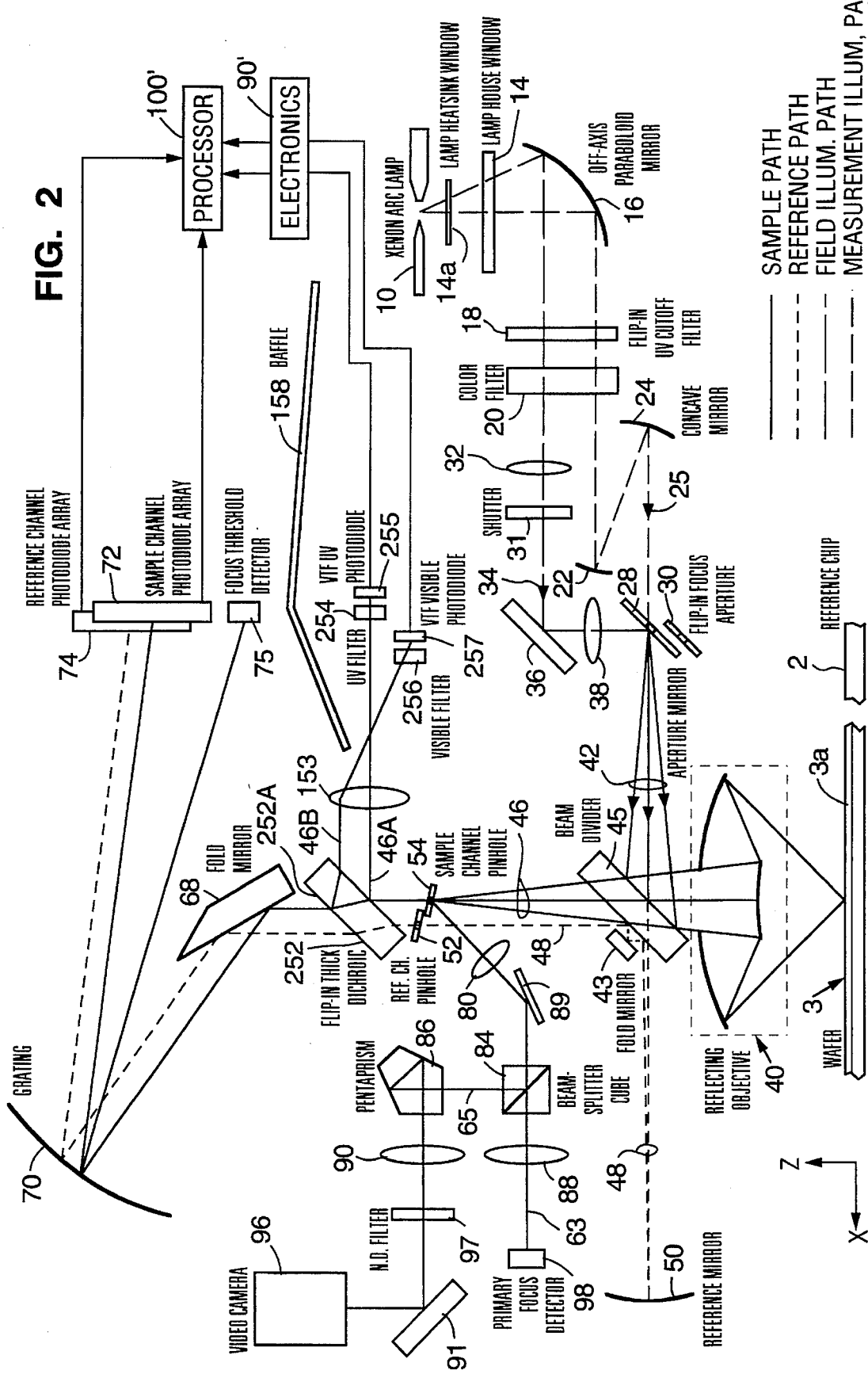
FIG. 2 is a schematic diagram of a preferred embodiment of the inventive broadband small spot spectral reflectometer, camera, and autofocus system.

An important advantage of the invention (including the preferred embodiment of the inventive system shown in FIG. 2) is reduction of the above-discussed problems with stability and sample-uniformity (i.e., micro-ripple in sample surface) in systems such as that shown in FIG. 1.

A key aspect of the invention is to separately detect both UV and visible radiation reflected from the sample. In preferred embodiments, the invention assumes that the visible radiation detector has a single effective wavelength which characterizes broadband visible radiation received thereby, and that the UV detector has a single effective wavelength which characterizes broadband UV radiation received thereby. The ratio of the measured UV to measured visible radiation from the sample is independent both micro-ripple effects and lamp fluctuations. Measuring the ratio of reflectance at two known wavelengths is just as useful as measuring absolute reflectance for determining thickness.

One disadvantage of measuring the ratio of reflectance at two known wavelengths (e.g., UV and visible) to determine film thickness in accordance with the invention is that some sensitivity may be lost (in comparison with the sensitivity attainable by absolute reflectance measurement at one wavelength), particularly when measuring thicker VTF films. However, the advantages of the invention more than overcome this disadvantage. We have found that the stability of measurements with the inventive system of FIG. 2 (using diodes 255 and 257) is improved by roughly a factor of two, and the precision is improved by roughly 25%, relative to measurements made with the FIG. 1 system (using diodes 93 and 95).

The inventive system has several additional advantages over systems such as that shown in FIG. 1: it is insensitive to drift between separate visible and UV channels during VTF measurements; it is much less sensitive to focus errors at high objective magnifications (e.g., 15×) because both reference and sample channels are affected similarly by focus; and lamp noise is better corrected (probably because radiation from both channels is collected from the same portion of the lamp arc and at the same angle). The radiation in both channels also travels through the same air mass, reducing the effect of air currents that can be a problem in operating a system of the type shown in FIG. 1.

A first preferred embodiment of the invention will be described with reference to FIG. 2. The elements of the FIG. 2 system that are identical to those of the above-described FIG. 1 system are numbered identically in both FIGS. 1 and 2. The description of these elements will not be repeated below with reference to FIG. 2.

The system of FIG. 2 differs from that of FIG. 1 in the following respects.

In an operating mode for measuring the thickness of very thin film 3a (VTF 3a) on wafer 3, the FIG. 2 system employs photodiodes 255 and 257 (rather than sample photodiode 93 and reference photodiode 95 of FIG. 1). Photodiodes 255 and 257 simultaneously receive portions of sample beam 46 (which has reflected from sample 3 and which includes frequency components from a broad range spanning at least a portion of the UV range and at least a portion of the visible range). Photodiode 255 generates a signal indicative of sample beam components in the UV band and photodiode 257 generates a signal indicative of sample beam components in the visible band. These two signals are processed in electronic circuitry 90', and then supplied to processor 100' which is programmed with software for processing them to produce an output signal indicative of an accurate measurement of the thickness of VTF 3a.

Sample beam 46 has frequency components in both the UV and visible ranges. Filter 254 transmits sample beam frequency components in the UV range (e.g., having wavelength in a range from 280 nm to 400 nm) to photodiode 255. Filter 256 transmits sample beam frequency components in the visible range (e.g., having wavelength in a range from 400 nm to 600 nm) to photodiode 257. In preferred embodiments, processor 100' determines a single "effective" wavelength for the UV radiation incident on photodiode 255 and a single "effective" wavelength for the visible radiation incident on photodiode 257.

Because they receive sample beam radiation, photodiodes 255 and 257 are sometimes denoted herein as "sample channel" detectors.

One function of flip-in dichroic mirror 252 (which is much thicker than flip-in dichroic 152 of FIG. 1) is to separate UV frequency components from visible frequency components of sample beam 46. For this reason, flip-in dichroic mirror 252 (or another optical element which performs the function of mirror 252 in an alternative embodiment of the invention), will sometimes be referred to herein as a "color separation means." The back face of mirror 252 has a broadband visible beamsplitter coating 252A while the front face (the bottom face in FIG. 2 and FIG. 3) has a dichroic mirror coating that reflects most of the incident UV radiation having wavelength in the range from about 280 nm (or 290 nm) to 400 nm but transmits most of the visible having wavelength above 400 nm. After sample beam 46 passes through the pinhole in plate 54, a UV portion thereof reflects from the front of dichroic 252 as beam 46A. Beam 46A is then focused by lens 153 onto photodiode 255. UV filter 254 in front of photodiode 255 removes residual visible light reflected by the dichroic coating. Filter 254 is preferably a color glass filter which blocks nearly all light between 400 nm and 700 nm. The limited transmission in the infrared can be tolerated.

The visible portion of sample beam 46 that is not reflected by the dichroic coating on the front face of mirror 252 travels through the mirror, and a portion thereof (40% in a preferred embodiment) is reflected by metallic beamsplitter coating 252A on the back face of mirror 252. The reflected light then exits the front of mirror 252 (near its top edge) as beam 46B. The transmitted light continues on through the spectrometer, reflects from mirror 68, and is used by zero order focus threshold detector 75 to determine if primary focus detector 98 has locked onto the correct peak. Detector 75 (which can be employed in the FIG. 1 system as well as the FIG. 2 system) is placed in the sample path zero-order beam to prevent primary focus detector 98 from locking onto a false minimum caused by patterns on wafer 3. Threshold detector 75 will have a very small signal unless primary focus detector 98 has locked onto the correct minimum.

Reflected beam 46B passes through the top of lens 153, and is refracted and focused onto photodiode 257. Filter 256 in front of photodiode 257 is designed to transmit to photodiode 257 only those frequency components of beam 46B in a band of wavelengths (roughly 200 nm wide) centered near 500 nm. In a preferred embodiment, filter 256 is made from two color glass filters bonded together.

Because the radiation incident on photodiodes 255 and 257 is filtered in fairly wide band-pass filters 254 and 256, processor 100' determines the described single effective wavelength for each photodiode in a simple manner (to be described below). If the radiation incident on photodiodes 255 and 257 were filtered in narrower band-pass filters (e.g., if each of filters 254 and 256 transmitted radiation in a wavelength band of about 60 nm), processor 100' could simply assume the effective wavelength for each photodiode to be the center of the band (e.g. having 60 nm width) transmitted by the corresponding filter. It is an important advantage of the invention that broadband (e.g., 200 nm wide) versions of filters 254 and 256 can be employed (with processor 100' determining a single effective wavelength for each detector 255 and 257), for measuring all film thicknesses in the VTF range, and for measuring a variety of samples (including, for example, samples having VTF films of silicon dioxide or silicon nitride).

The data from photodiode 255 (and photodiode 257) can be collected in the same manner as the data from detectors 93 and 95 in FIG. 1, using the same electronics. Photodiodes 255 and 257 (and optional photodiodes 355 and 357) are operated in the photovoltaic mode. Their output signals first pass through dual high-gain, low-noise transimpedance amplifiers (not separately shown) located inside the spectrometer housing. If photodiodes 355 and 357 are provided, a multiplexer can be connected to receive the output of the amplifiers, to switch between the amplified outputs of sample path photodiodes 255 and 257 and reference path diodes 355 and 357. The amplified analog signals then travel to measurement control board 90' via coax cable where they pass through dual lowpass filters, dual signal dividers, dual amplifiers, and dual 16-bit A-to-D converters. The output of the A-to-D converters on board 90' can be written into FIFO buffers mounted on a single, common board with processor 100', and then read from the FIFO buffers by processor 100'. The communication between measurement control board 90' and the board on which processor 100' is mounted is done with fiber optics to reduce the risk of ground loops adding noise to the analog signals being processed.

During a typical measurement, data points are collected from each diode (255 and 257 and optionally also 355 and 357) over simultaneous 600 millisecond intervals. The value 600 msec was chosen because it is an even multiple of both 50 hz and 60 hz line noise. It also fortunately is roughly one period of typical xenon lamp noise. The programmed processor 100' then averages the points for each diode, subtracts the darknoise DC level for each diode (darknoise is measured before each set of wafer measurements by leaving nothing under objective 40 and recording the reading), and divides the result for UV diode 255 by the result for visible diode 257 to obtain a measurement of wafer 3. The resulting value is proportional to the ratio of UV to visible reflectance for the wafer, and, with calibration and optical constants for the wafer, can be converted directly into film thickness. The calibration and thin film determination process is described below.

Figure 3:
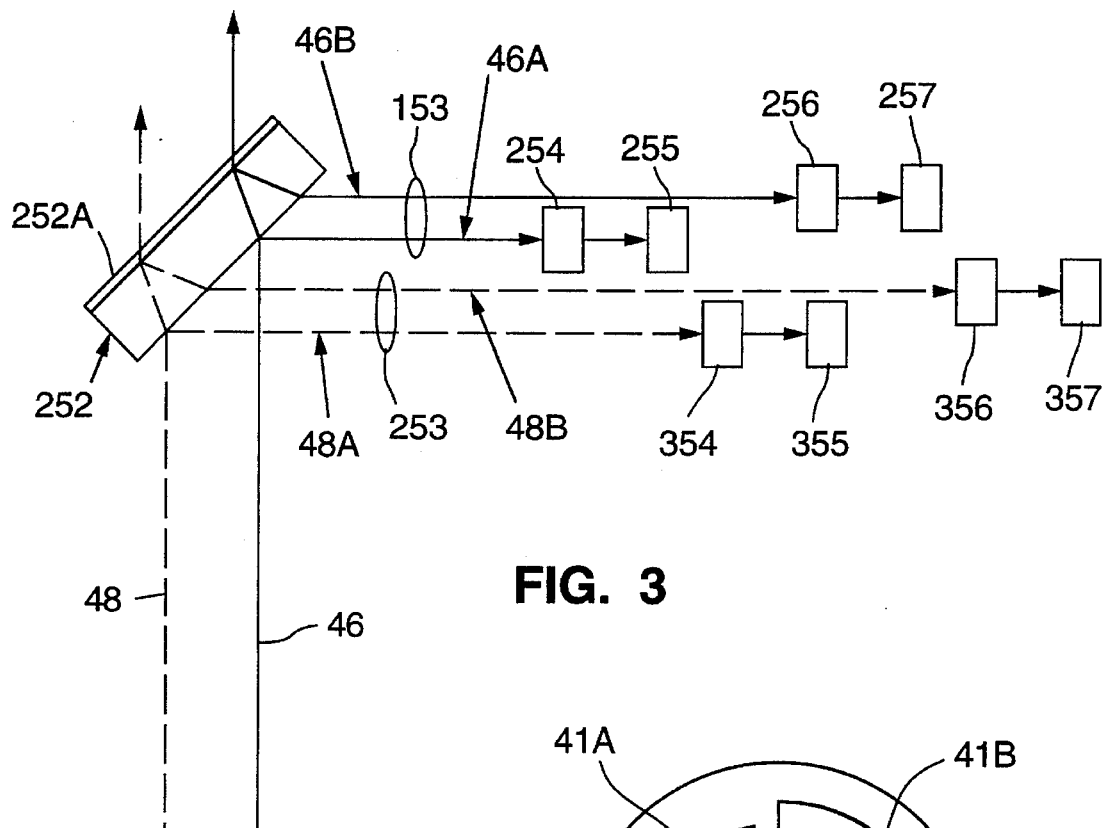
FIG. 3 is a schematic diagram of a portion of an alternative embodiment of the inventive system (a variation on the system shown in FIG. 2).

The FIG. 2 system optionally also includes two reference channel detectors, such as photodiodes 355 and 357 as shown in FIG. 3, in addition to sample channel detectors 255 and 257. As shown in FIG. 3, sample beam 46 (reflected from sample 3) and reference beam 48 (which has not reflected from sample 3) are incident at thick dichroic mirror 252. As described above with reference to FIG. 2, portions 46A and 46B of sample beam 46 reflect from mirror 252, are filtered in filters 254 and 256, and are then incident on sample channel detectors 255 and 257.

Similarly, a portion of reference beam 48 (comprising UV radiation) reflects from the front surface of mirror 252 as beam 48A. Beam 48A is then focused by lens 253 onto photodiode 355. UV filter 354 in front of photodiode 355 removes residual visible light reflected by the dichroic coating. Filter 354 is preferably a color glass filter which blocks nearly all light between 400 nm and 700 nm. The limited transmission in the infrared can be tolerated.

The visible portion of reference beam 48 that is not reflected by the dichroic coating on the front face of mirror 252 travels through the mirror, and a portion thereof (40% in a preferred embodiment) is reflected by metallic beamsplitter 252A coating on the back face of mirror 252. The reflected light then exits the front of mirror 252 as beam 48B. The transmitted light continues on through the spectrometer, and reflects from mirror 68. Reflected beam 46B passes through lens 253, and is refracted and focused by lens 253 onto photodiode 357. Filter 356 in front of photodiode 357 is designed to transmit to photodiode 357 only those frequency components of beam 48B in a band of wavelengths (roughly 200 nm wide) centered near 500 nm. In a preferred embodiment, filter 356 is made from two color glass filters bonded together.

Because the radiation incident on photodiodes 355 and 357 is filtered in fairly wide band-pass filters 354 and 356, processor 100' determines a single effective wavelength for each of these photodiodes in a simple manner (to be described below). If the radiation incident on photodiodes 355 and 357 were filtered in narrower band-pass filters (e.g., if each of filters 354 and 356 transmitted radiation in a wavelength band about 60 nm in width), processor 100' could simply assume the effective wavelength for each photodiode to be the center of the band (e.g. having 60 nm width) transmitted by the corresponding filter.

Reference detector 355 generates a signal indicative of reference beam components in the UV band. Reference detector 357 generates a signal indicative of reference beam components in the visible band. By processing these two signals, as well as the two signals from sample channel detectors 255 and 257, programmed processor 100' can even more accurately determine the thickness of very thin film 3a on sample 3. Use of detectors 355 and 357 (as well as detectors 255 and 257) can avoid error caused by change in vertical position of the arc of lamp 10 (which in turn changes the ratio of UV to visible incident beam divider 45 because the arc in its new position would have a different temperature) by providing the data needed for processor 100' to divide out the effect of a change in the lamp spectrum. Alternatively, this source of error can be avoided by designing the housing of lamp 10 to be very stable.

It may be necessary to compensate for inconsistent quality and reflectance of metallic beamsplitter coating 252A. For example, it may be necessary to change the gain of the visible channel amplifier on a measurement control board to accomplish this compensation. Preferably, resistors that set the gain are installed with sockets on the board. A metallic coating 252A is preferred over a more conventional dielectric coating to reduce the sensitivity of the system to polarization. In some applications, polarization may not be an important variable to control, so that a dielectric coating can be substituted for metallic coating 252A.

It has been recognized that there is an inherent problem in the FIG. 1 system, in that a significant amount of visible light reflecting from the back surface of dichroic 152 typically falls on photodiodes 93 and 95. This tends to lengthen the effective wavelength incident on the photodiodes, decreasing sensitivity to film thickness. The FIG. 1 system typically employed small photodiodes 93 and 95 which somewhat difficult to align. The FIG. 2 system has much purer color separation than the FIG. 1 system, and preferably employs photodiodes 255 and 257 which are much larger than diodes 93 and 95, to reduce or eliminate these problems.

In the FIG. 2 system, baffle 158 is preferably positioned between the diodes (diodes 255 and 257, and optionally also reference channel diodes 355 and 357 shown in FIG. 3) and grating 70 to shield the diodes from the −1 order diffracted spectrum of grating 70.

Preferably, diodes 255 and 257 (and optionally also reference channel diodes 355 and 357) are bonded to a copper block and temperature controlled with thermoelectric coolers to avoid changes in the dark current level that might cause measurements to drift.

It should be appreciated that some variations of the inventive system will not include elements 68, 70, 72, 74, and 75 of FIG. 2.

We will describe calibration and measurement steps performed in accordance with the invention to obtain true reflectance measurements using photodiodes 255 and 257. However, before describing this aspect of the inventive method, we will describe preferred calibration and measurement steps performed to obtain true reflectance measurements using photodiodes 93 and 95 of the FIG. 1 system.

With reference to FIG. 1, because it is very difficult to measure the precise radiation intensity both before and after the radiation reflects from sample 3, most absolute reflectance measurements are made by comparing unknown sample 3 to a standard (reference chip 2). Reference chip 2 is typically a silicon wafer with a thin layer of silicon dioxide.

Comparisons of unknown samples to a standard (chip 2) must be made sufficiently often so that drift between the sample and reference channel paths does not introduce significant error. For this reason reference chip 2 is placed on a corner of the stage on which each sample 3 rests, and chip 2 is measured before measurements are made on each sample 3. However, reference chip 2 cannot be used as an absolute or permanent standard for two reasons: first, there is usually some tilt or curvature of chip 2 due to bonding it in place that effects the reflected signal slightly; second, and more importantly, it is impossible for the apparent film thickness to stay constant to a couple of angstroms over the life of the machine. Particles and contamination build up and cannot always be completely cleaned off. Even the process of cleaning chip 2 can effect its surface enough to change its reflectance. Therefore we must periodically calibrate reflectance by comparing reference chip 2 to a well-characterized calibration wafer (not shown) placed on the stage. The calibration wafer is typically a silicon wafer with a known thickness of silicon dioxide (measured ellipsometrically). The reflectance of the calibration wafer is calculated accurately from the thickness and optical constants of the materials which comprise it.

We then must calibrate the effective wavelength of VTF detector 93 (and VTF detector 95). The reflectance calibration must be done first before the effective wavelength calibration. During reflectance calibration, the reading from the calibration wafer is divided by the reading from reference chip 2 and stored in a file (e.g., in processor 100) along with the predetermined optical constants and thickness for the calibration wafer (each "reading" is a result of subtracting the darknoise from the sample and signal channels and then dividing the sample by the reference channel). The effective wavelength calibration requires a second well-characterized wafer (not shown in the figures) with a different film thickness. The readings from this second wafer and reference chip 2 are divided as in the previous calibration. By multiplying this ratio by the inverse of the ratio stored from the reflectance calibration, we obtain the ratio of the reflectances of the two calibration wafers independent of changes in system transmission that may have occurred between the two measurements. Since we know the theoretical reflectance spectra of the two calibration wafers, it is an easy matter for processor 100 to determine the one particular wavelength that should produce the observed ratio of reflectances. This effective wavelength is then stored in the calibration file (e.g., within processor 100) and is used later both to calculate the actual reflectance of the reflectance calibration wafer, and to convert the measured reflectance of sample wafers 3 into thickness. The effective wavelength of VTF detector 93 (and 95) is typically between 350 and 370 nm.

We next explain in more detail the processing steps performed by processor 100 to determine the effective wavelength of detector 93 (or 95). Given a known film thickness, T, and a known wavelength L, there is a function R(L, T) that determines the reflectance of that film at that thickness and wavelength. This function is described in P. S. Hauge, "Polycrystalline Silicon Film Thickness Measurement from Analysis of Visible Reflectance Spectra," Journal of the Optical Society of America, Vol. 69, No. 8, pp. 1143–1152 (1979). The optical constants of the substrate and film type are also variables in the function R(L,T), but it can be assumed that they remain constant throughout the calibration procedure.

To calibrate, two wafers with film thicknesses T1 and T2, respectively, are measured. The following four quantities are measured: I1=measured intensity value from the first calibration wafer, I2=measured intensity value from the second calibration wafer, ICHIP1'=reading taken from reference chip 2 just prior to measuring the first calibration wafer, and ICHIP2'=reading taken from reference chip 2 just prior to measuring the second calibration wafer.

Each of these four measured values is preferably found by performing the following operation: I=(sample channel intensity−darknoise)/(reference channel intensity−darknoise). Alternatively (where the reference channel is not present, or not used), each of the four measured values can be found by performing the following operation: I=(sample channel intensity−darknoise).

The following values are then determined:

I1/ICHIP1'=A[R($L_{eff}$, T1)], and

I2/ICHIP2'=A[R($L_{eff}$, T2)], where A is a constant, and $L_{eff}$ is the unknown effective wavelength. Given these two independent equations with two unknowns (A and $L_{eff}$), processor 100 easily solves them numerically to find $L_{eff}$.

The equation used to find reflectance, R, of sample wafer 3 (at the effective wavelength) is then:

R=(ISAMP/ICHIP2)(ICHIP1/ICAL)(RCAL), where:

ISAMP'=Reading taken on sample wafer 3;

ICHIP2=Reading taken on reference chip 2 just prior to measuring sample;

ICHIP1=Reading taken on reference chip 2 during reflectance calibration and stored in the calibration file;

ICAL=Reading taken on the reflectance calibration wafer and stored in the calibration file; and RCAL=Theoretical reflectance of the calibration wafer at the effective wavelength (calculated by processor 100 from the known film thickness, optical constants, and the effective wavelength. The film thickness and optical constants of the calibration wafer are stored in the calibration file).

It should be appreciated that each reading (e.g., ISAMP') is actually the sample channel signal (the output of detector 93) divided by the reference channel signal (the output of detector 95) with noise subtracted from both signals.

In contrast with the foregoing description of calibration of detectors 93 and 95, and processing of their output, detectors 255 and 257 (and optionally also 355 and 357) are calibrated and their output processed as follows. There are two basic differences between calibration of and measurement using detectors 93 and 95 and the corresponding operations using detectors 255 and 257. The first is that all quantities measured and calculated with detectors 255 and 257 are ratios of UV to visible. The second is that there is a second effective wavelength calibrated for visible detector 257 (different from the effective wavelength calibrated for UV detector 255). Once the two effective wavelengths are found, the equation used to find the ratio of UV to visible reflectance on the sample is:

R=(ISAMP/ICHIP2)(ICHIP1/ICAL)(RCALUV/RCALVIS), where:

R=Ratio of UV to visible reflectance of sample 3;

ISAMP=Measured UV intensity divided by measured visible intensity on sample 3;

ICHIP2=Measured UV intensity divided by measured visible intensity on reference chip 2 just prior to measuring sample 3;

ICHIP1=Measured UV intensity divided by measured visible intensity on reference chip 2 during reflectance calibration and stored in a calibration file within processor 100';

ICAL=Measured UV intensity divided by measured visible intensity on a reflectance calibration wafer and stored in the calibration file.

RCALUV=Theoretical reflectance of the calibration wafer at the UV effective wavelength (it is calculated from the known film thickness, optical constants, and the UV effective wavelength. The film thickness and optical constants of the reflectance calibration wafer are stored in the calibration file);

RCALVIS=Theoretical reflectance of the calibration wafer at the visible effective wavelength (it is calculated from the known film thickness, optical constants, and the visible effective wavelength. The film thickness and optical constants of the reflectance calibration wafer are stored in the calibration file).

Each intensity measurement (ISAMP, ICHIP2, ICHIP1, and ICAL) preferably has the darknoise DC level subtracted therefrom.

Processor 100' can process the ratio value, R, of UV to visible reflectance along with the optical constants to solve numerically for film thickness. The above-cited paper by P. S. Hauge, "Polycrystalline Silicon Film Thickness Measurement from Analysis of Visible Reflectance Spectra," Journal of the Optical Society of America, Vol. 69, No. 8, pp. 1143–1152 (1979), describes a method by which film thickness can be computed from measured reflectance data, where the reflected radiation has a single wavelength. This method (and variations thereon) can be implemented by processor 100' in performing preferred embodiments of the present invention, since such embodiments assume a single effective wavelength of the reflected radiation in each of two wavelength bands (e.g., UV and visible bands).

The reflectance calibration data are collected before the other two calibrations are done, and the raw data and calibration wafer constants are stored in the calibration file within processor 100'.

After reflectance calibration, the UV effective wavelength calibration is done on a second "known" wafer (having known characteristics, including a different, known, film thickness). If the FIG. 2 system is being calibrated for the first time, a nominal value is first entered for the visible effective wavelength. The numerical calculation (performed within processor 100') involves finding the one UV effective wavelength that produces a match when it is used both for calculating the theoretical reflectance ratios on the two calibration wafers, and when it is used to calculate reflectance ratios from the measurements of the two "known" wafers.

The visible effective wavelength calibration (also known as reference diode calibration) is next performed, but only if it has never been done before. The VTF measurement accuracy does not depend critically on the exact visible wavelength value (although the result of the UV wavelength calibration will be affected by the visible wavelength value). It therefore only needs to be calibrated once (e.g., at the factory) or if critical optical components (such as dichroic 252 or visible filter 256) are replaced. The calibration is done by measuring a third "known" wafer. The visible wavelength calibration actually finds both wavelengths. The software (programmed processor 100') iteratively alters both effective wavelengths so that the theoretically calculated reflectance ratios for all three calibration wafers match the reflectance ratios calculated from the stored calibration measurements.

Processor 100' preferably determines the UV effective wavelength and the visible effective wavelength in the following manner (similar but not identical to the above-described manner in which processor 100 can determine the effective wavelength of the UV radiation incident on photodiode 93 and 95). Processor 100' processes values measured on three wafers with known film thicknesses, T1, T2, and T3, respectively. Specifically, the following values are measured: I1=measured intensity value from the first calibration wafer, I2=measured intensity value from the second calibration wafer, I3=measured intensity value from the third calibration wafer, ICHIP1'=reading taken from reference chip 2 just prior to measuring the first calibration wafer, ICHIP2'=reading taken from reference chip 2 just prior to measuring the second calibration wafer, and ICHIP3'=reading taken from reference chip 2 just prior to measuring the third calibration wafer.

Each of these six measured values is typically found by performing the following operation: I=(UV channel intensity−darknoise)/(visible channel intensity−darknoise). However, where the system also has UV and visible detectors in a reference path (e.g., detectors 355 and 357 of FIG. 3), each of the six measured values is preferably found by performing the following operation: I=(UV sample channel intensity−darknoise)(visible reference channel intensity−darknoise)/[(visible sample channel intensity−darknoise)(UV reference channel intensity−darknoise)].

The following values are then determined:

I1/ICHIP1'=A[R($L_{uv}$, T1)]/A[R($L_{vis}$, T1)],

I2/ICHIP2'=A[R($L_{uv}$, T2)]/A[R($L_{vis}$, T2)], and

I3/ICHIP3'=A[R($L_{uv}$, T3)]/A[R($L_{vis}$, T3)], where A is a constant, $L_{uv}$ is the unknown effective UV wavelength, and $L_{vis}$ is the unknown effective visible wavelength. Given these three independent equations with three unknowns (A, $L_{uv}$, and $L_{vis}$), processor 100' can readily solve them numerically to find $L_{uv}$ and $L_{vis}$. If $L_{vis}$ is known, it is only necessary to measure two calibration wafers and solve two of the above equations to find $L_{uv}$.

Typically, when performing the entire sequence of three calibrations, the reflectance calibration is done on a roughly 90 A to 140 A oxide wafer, the UV wavelength calibration is done on a roughly 20 A to 40 A oxide wafer, and the visible wavelength calibration is done on a roughly 170 A to 220 A wafer. When the routine two-wafer calibration sequence is done later, the 170 A to 220 A wafer is used for reflectance calibration and the 20 A to 40 A wafer for UV effective wavelength determination. The best accuracy is obtained when the calibration wafer thicknesses are spaced far apart near the ends of the measurement range. There is actually no fundamental reason why the thin (20 A to 40 A) wafer cannot be used for reflectance calibration and the thick (170 A to 220 A) wafer for UV effective wavelength calibration.

Before performing the three-wafer calibration sequence, the thicknesses of all three "known" wafers must be known extremely accurately. If a value only wrong by a few angstroms (A) is entered for one of the wafers, then during the visible wavelength calibration it may be impossible to converge on a solution for the two effective wavelengths. If a solution is found, the two wavelengths may have unrealistic values. Practically, as long as a solution is found, the measurement inaccuracy will only be as large as the inaccurate value entered for the calibration wafer, but the unrealistic wavelengths are a clue that the calibration is not good. Since the visible effective wavelength calibration is done only once, it is important that it be good. During the routine two-wafer calibration sequence, a two angstrom (2 A) error, for example, in one of the wafers will not change the UV effective wavelength very much, but there will still be a two angstrom error at that end of the measurement range.

Maintaining the calibration wafers requires either carefully controlled environmental conditions or frequent re-measurement. Silicon dioxide on silicon wafers can be used for calibration where sample 3 to be measured is of that type. However, silicon dioxide can absorb water causing the refractive index to increase and the apparent thickness to change. Wafers that are cleaned with water and stored in a clean environment will appear to decrease in thickness by a couple of angstroms over several days as the water is de-absorbed. Wafers stored in a dirty environment will appear to increase in thickness as particles and organic films accumulate. Variations in humidity cause the apparent thickness to change by up to 2 A. A new "bare" silicon wafer will have an increase in true oxide thickness for a week or more as native oxide continues to grow. Certain types of wafer carriers may outgas over long periods of time and add films to the wafers. Finally, if one particular site on a wafer is measured with the 15× objective 100 times, the exposure to UV light will grow about 2 A of oxide. The intensity incident on the wafer at 1× is lower and the effect has not been noticed with an objective of that low magnification. For all these reasons, it is important that the calibration wafers be measured frequently using a good ellipsometer. It is the apparent thickness that must be known for calibration purposes, and that can be measured because ellipsometers are sensitive to all these effects in exactly the same way.

In a typical, well-calibrated system (including the described lamp), the UV effective wavelength is about 35 Onm (for both 1× and 15× objective lenses). The visible effective wavelength is about 550 nm for a 1× objective and about 500 nm for a 15× objective. The different visible wavelengths found for the two objectives automatically compensate for the larger numerical aperture of the 15× objective. A high N.A. objective collects light at large angles of incidence and would produce measurements that were too thin if not compensated. The FIG. 2 system does not need to use the same N.A. correction algorithm used with standard film thickness measurements.

It may be impractical to design a specific implementation of the FIG. 2 system optics for a UV effective wavelength much shorter than 350 nm without a significant intensity loss. A typical implementation of the FIG. 1 system does not have as pure color separation as does the FIG. 2 system, and thus its effective wavelength is typically about 365 nm.

There are several other hardware features important to a preferred implementation of the FIG. 2 system. One important feature (to be described below with reference to FIGS. 4–8 are that the 1× and 15× pupil stops (of objective 40) are rotated by 180 degrees (relative to their orientation in the FIG. 1 system).

Another feature is that lamp housing window 14 is preferably made very thin to reduce chromatic aberration in the measurement illumination path. This chromatic aberration causes the UV and visible images of the arc of lamp 10 projected onto aperture mirror 28 to separate, creating problems with the 15× focus curve (to be discussed below).

Another feature is that means for adjusting the lamp housing's position along the z-axis shown in FIG. 2 should hold the lamp very steadily. If the lamp position drifts while measuring a wafer, the ratio of UV to visible radiation changes and the measurements may drift.

Next, the preferred orientation of the pupil stops of objective element 40 will be described with reference to FIGS. 4–8. The discussion contemplates that objective element 40 includes one or more objectives mounted on a rotatable turret which allows a selected one of the objectives to be placed in the path of sample beam 46. For example, the following three objectives can be mounted on the turret: a 15× Schwarzchild design all-reflective objective; a 4× Nikon CFN Plan Apochromat (color corrected at three wavelengths), and a 1× UV transmissive objective.

As shown in FIGS. 4–7, objective lens 141 (of objective element 40) and pupil stop 41 (of objective element 40) are positioned in the path of sample beam 46. Beam 46 reflects from beam divider 45, and portions of reflected beam 46 then pass through a first subset of the apertures (either apertures 41A or 41B) of pupil stop 41. The radiation passing through the pupil stop apertures is focused by lens 141 onto sample 3, reflects from sample 3, again passes through lens 141, and portions of the radiation transmitted through lens 141 then pass through another subset of pupil stop 41's apertures.

Figure 8:
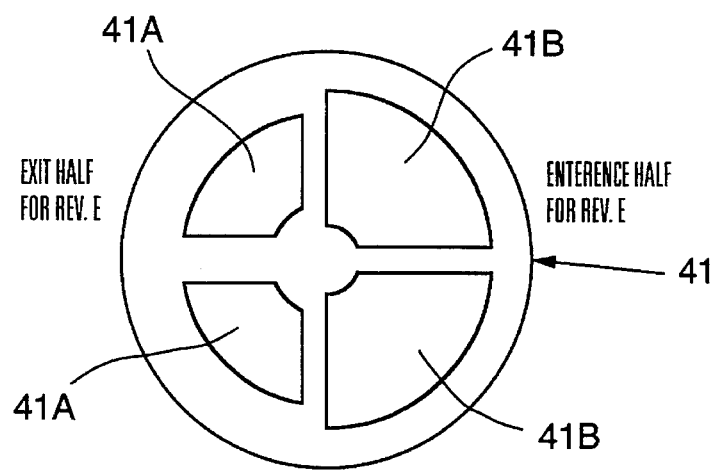
FIG. 8 is a top elevational view of pupil stop 41 of FIGS. 3 through 6.

FIG. 8 is another view of pupil stop 41 which shows the two sets of apertures which extend through it: two relatively small apertures 41A; and two relatively large apertures 41B.

Figure 4:
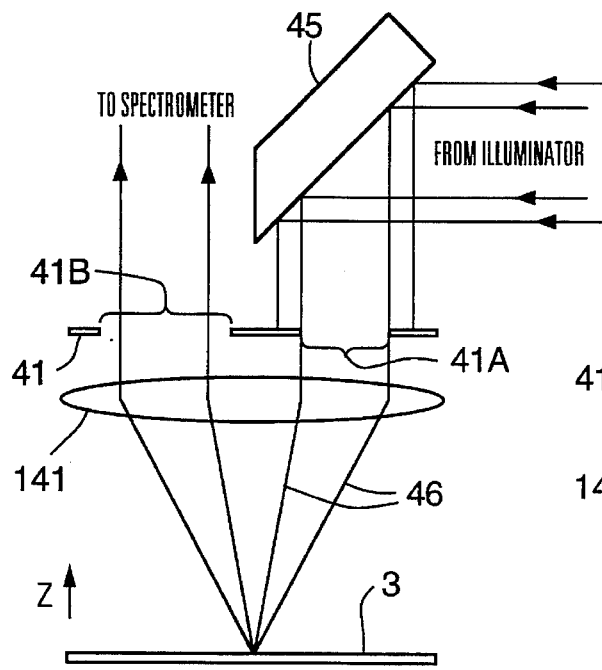
FIG. 4 is a simplified cross-sectional view of a portion of beamsplitter mirror 45 (of FIG. 2), and a portion of objective 40 (of FIG. 2) positioned non-optimally relative to mirror 45.
Figure 5:
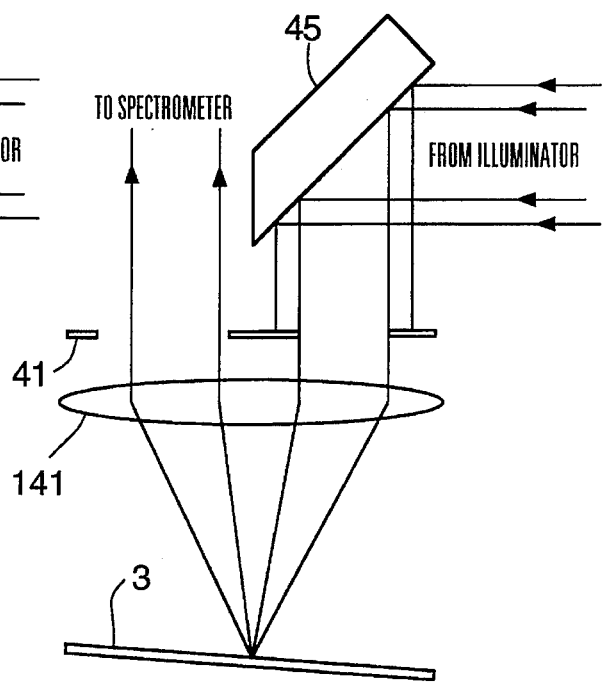
FIG. 5 is a simplified cross-sectional view of the beamsplitter mirror portion and objective portion of FIG. 4, showing their placement relative to a tilted wafer.
Figure 6:
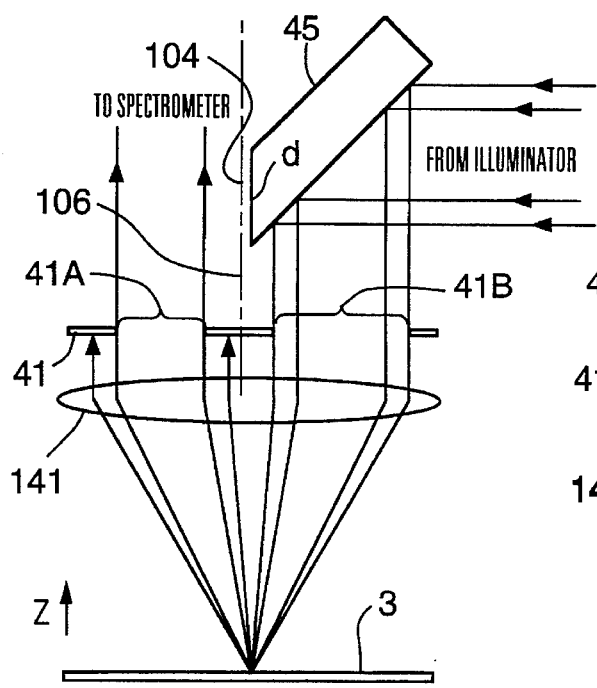
FIG. 6 is a simplified side cross-sectional view of a portion of beamsplitter mirror 45, and a portion of objective 40 positioned optimally relative to mirror 45.
Figure 7:
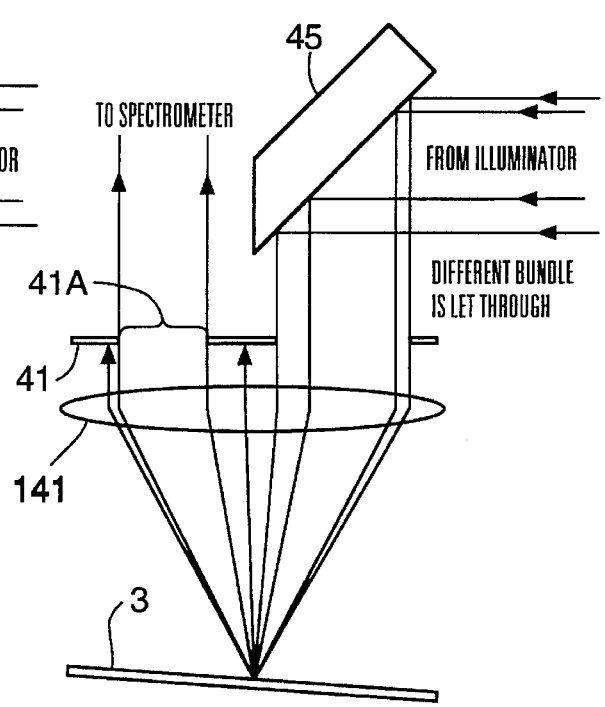
FIG. 7 is a simplified side cross-sectional view of the beamsplitter mirror portion and objective portion of FIG. 6, showing their placement relative to a tilted wafer.

FIGS. 4 and 5 show pupil stop 41 in a non-optimal orientation relative to beam divider 45. FIGS. 6 and 7 show pupil stop 41 oriented relative to beam divider 45 in a preferred orientation in accordance with the invention.

The non-optimal orientation of pupil stop 41 in FIGS. 4 and 5 can be changed to the preferred orientation of FIGS. 6 and 7 by rotating pupil stop 41 by 180 degrees about the z-axis. The inventive orientation of pupil stop 41 (shown in FIGS. 6 and 7) dramatically increases the insensitivity of the FIG. 2 system to ripple on the surface of sample 3 (e.g., micro ripple in the thickness of a thin film coating on sample 3), which dramatically improves the system performance and eliminates the need for optimizing the focus position for best ripple insensitivity.

Until the invention, pupil stop 41 was oriented as in FIG. 4, in order to reduce the system sensitivity to wafer tilt. As shown in FIG. 4 (and FIG. 5), beam 46 enters the objective element (from beam divider 45) through the constricted half of pupil stop 41 (i.e., through relatively small apertures 41A), reflects off wafer 3, and exits the objective element through the enlarged half of pupil stop 41 (i.e., through relatively large apertures 41B). In this configuration, larger apertures 41B allow radiation from a slightly tilted wafer (e.g., wafer 3 in the tilted position shown in FIG. 5) to be collected without attenuation.

As shown in FIG. 6 (and FIG. 7), beam 46 enters the objective element from beam divider 45 through the enlarged half of pupil stop 41 (i.e., through relatively large apertures 41B), reflects off wafer 3, and exits the objective element through the other half of pupil stop 41 (i.e., through relatively small apertures 41A). In the FIG. 6 orientation of pupil stop 41, insensitivity to wafer tilt is maintained as long as the illumination entering the objective element is uniform across the pupil. If wafer 3 is tilted slightly (as shown in FIG. 7), a larger halfcone of radiation reflected from wafer 3 will shift on the constricted exit half, but as long as the illumination (from beam divider 45) is uniform the total amount of radiation passing through relatively small apertures 41A and leaving the objective will remain the same as in the case of an untilted wafer (as shown in FIG. 6).

The FIG. 6 orientation of stop 41 cannot be used with most conventional microscope illuminators because the light source (filament or arc), which is inherently non-uniform, is imaged onto the pupil to produce the best uniformity at the field plane. However, in the inventive system of FIG. 2, the arc of lamp 10 is imaged onto the field plane, and the pupil plane is uniform.

The reason that the inventive pupil stop orientation of FIG. 6 helps increase the system's insensitivity to wafer ripple, can be understood by considering what happens as light reflects off a rough (rippled) wafer surface. A single ray reflecting off the rough surface will be scattered into a lobe of light where the greatest intensity lies along the usual angle of reflection and the intensity drops off as the angle varies from that. Wafer topography that is much broader than a wavelength of the light and only a few nanometers deep (such as micro ripple) reflects light into a narrow lobe depending on amplitude and spatial frequency. Features that are comparable in size to a wavelength will scatter light into much rounder lobes.

Figure 9:
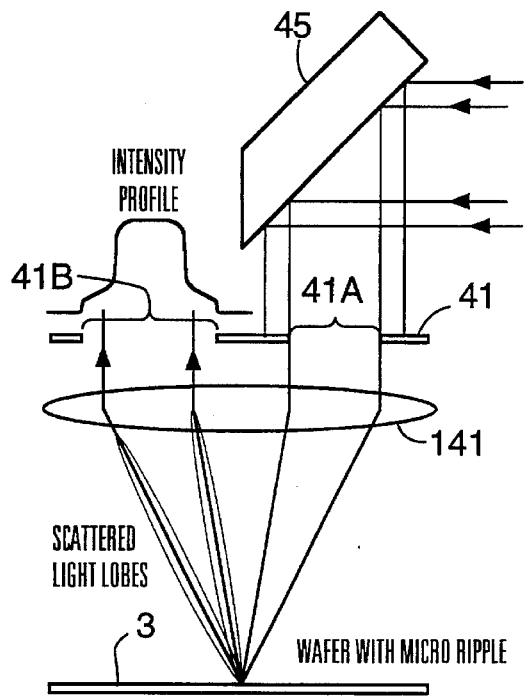
FIG. 9 is identical to FIG. 4, except that it also includes representations of reflected beam intensity profiles.
Figure 10:
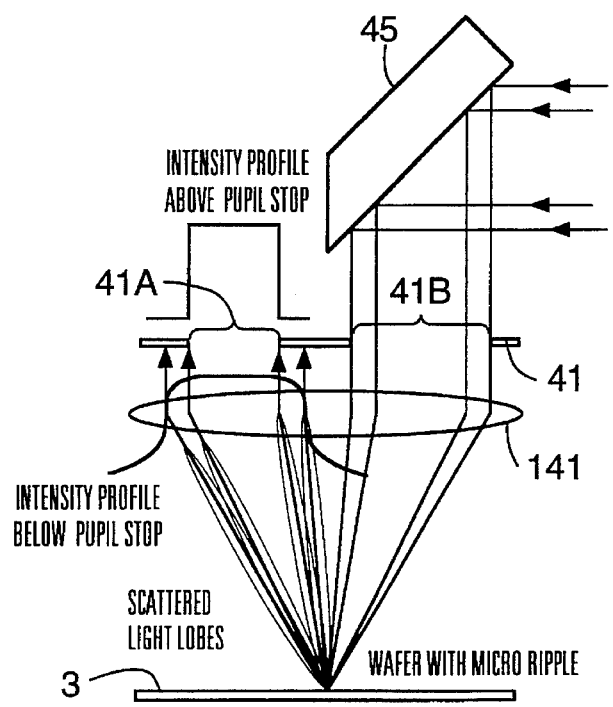
FIG. 10 is identical to FIG. 6, except that it also includes representations of reflected beam intensity profiles.
Figure 11:
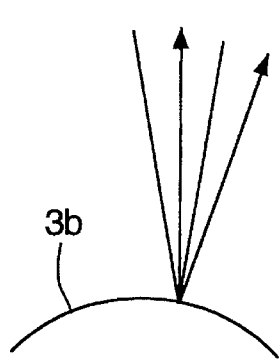
FIG. 11 is a diagram of radiation reflecting from a small ripple on the surface of sample 3.
Figure 12:
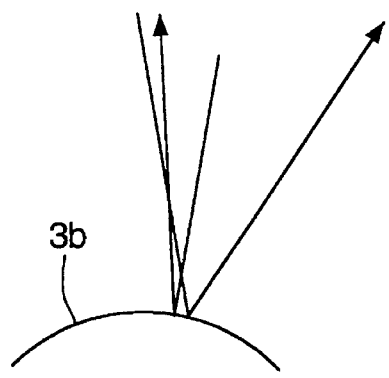
FIG. 12 is another diagram of radiation reflecting from a small ripple on the surface of sample 3.

As shown in FIG. 9, if the exit half of the pupil stop includes relatively large apertures 41B (as described with reference to FIG. 4), the edges of exit apertures 41B will block the more widely scattered rays. The exact amount of light blocked will depend critically on the width of the lobes and amount of ripple on the wafer (which determine the curved shape of the transmitted "intensity profile" shown in FIG. 9). However, if (as shown in FIG. 10) the exit half of the pupil stop includes relatively small apertures 41A (as described with reference to FIG. 6), the edges of exit apertures 41A will block the light in a region that remains at constant intensity with minor amounts of scattering (i.e., the transmitted "intensity profile" shown in FIG. 10 is substantially flat across exit aperture 41A), and the system will be less sensitive to wafer micro ripple. Until the present invention, it was necessary to fine tone the focus position because micro ripple on the wafer surface acts as a set of curved mirrors. When the illuminator aperture mirror 28 is projected precisely on curved surface 3b (a feature on the rippled surface of wafer 3), the entire cone of reflected light may be diverted (which is the cause of scattering), but the subtended angle of the cone emanating from a single point on surface 3b will not vary (as shown in FIG. 11). If, on the other hand, autofocus normally leaves the image of aperture mirror 28 either slightly above or slightly below surface 3b of a generally flat (but micro rippled) wafer, then the wafer curvature will change the spread of the reflected cone (as shown in FIG. 12). That change in spread with focus position simply tends to aggravate the effect of scattering. The inventive pupil stop orientation (of FIG. 6) makes the FIG. 2 system less sensitive to this effect as well.

One disadvantage of putting the constricted half of pupil stop 41 on the exit side (as in FIG. 6) is that resolution of wafer patterns is slightly reduced. In the previous orientation (as in FIG. 4), even though wafer 3 was illuminated through the constricted pupil with a small N.A., the larger exit pupil allowed a larger N.A. to collect light scattered from pattern edges. With the inventive pupil stop orientation (of FIG. 6), the N.A. of light collected from the wafer is restricted.

As a practical matter, when retrofitting a system of the FIG. 4 type (to include the FIG. 6 feature of the invention in the retrofitted system), each objective lens 141 and corresponding pupil stop 41 typically cannot simply be rotated 180° about the z-axis without modification. This is because the knife edge of beam divider 45 does not lie exactly on the optical axis, but is typically set back (e.g., by 0.8 mm) to avoid vignetting the field illumination. This means that the larger entrance half of pupil stop 41 is not fully filled, and one edge of the reflected cone may not be completely blocked by the constricted exit half of pupil stop 41. To compensate, the horizontal spider of the pupil stop will typically need to be widened.

To clarify the explanation in the preceding paragraph, with reference to FIG. 6, beamsplitter mirror 45 is placed with its edge 104 a slight distance, d, which is about 0.4 to 1.2 mm (and typically 0.8 mm) from optical axis 106 of objective 40, to prevent beamsplitter mirror 45 from vignetting the reflected sample beam 46 when a wide field of view is used. Edge 104 is preferably an acutely angled edge to avoid interference between the side of beamsplitter mirror 45 and the reflected sample beam 46.

One of the advantages of invention is that normally the ratio of UV to visible signals (the ratio of the output intensities of photodiodes 255 and 257) versus focus is flatter than the UV signal alone (e.g., the output intensity of photodiode 255 or 93 alone) plotted versus focus. If the ratio is flat for focus positions near best focus, the measured thickness will not be significantly affected by small focus errors. The shape of the focus curve (detected intensity or intensity ratio, versus focus position) can vary, but usually resembles a third-order polynomial.

The shape and position of the focus curve can be adjusted to position either the minimum, maximum, or inflection point at best focus, primarily by adjusting the position of lamp 10 (it should be explained that both FIG. 1 and 2 are schematic. In FIG. 1 and FIG. 2, lamp 10 is shown oriented horizontally in the plane of the Figure (for convenience), whereas it should be oriented perpendicularly to the plane of the Figure to be consistent with the orientation of the other illuminator assembly components. If lamp 10 is oriented perpendicularly to the plane of FIG. 2, then shape and position of the focus curve can be adjusted to position either the minimum, maximum, or inflection point at best focus by adjusting the left/right position of lamp 10 (i.e., the position of lamp 10 along the x-direction in FIG. 2). The lamp position has an effect because the gradient of intensity across the arc also corresponds to a gradient of temperature. Higher temperature corresponds to a higher proportion of UV radiation. As the z-stage (the stage for supporting sample 3, which is movable along the z-axis) scans from low to high z position, the image of aperture mirror 28 (onto which the arc is focused) appears to scan across the pinhole through plate 54 from top to bottom on video monitor 96 (this scanning motion is due to the fact that a cross-section through the cone of light focused on the sample is in the shape of a half annulus). Moving the lamp to the left or right along the x-axis moves the image of the arc vertically on the monitor, thus changing the gradient of UV and visible light scanned across the pinhole as focus is scanned. Moving the lamp to the left or right tends to shift the peak z-position of the UV and visible signals, and also tends to move the extrema of the focus curve diagonally towards or away from each other. Moving the lamp vertically tends to change the separation of the focus curve extrema in the vertical direction, but it can also add noise or make the detected signals too weak or too strong. When the focus curve is adjusted, the peak of the UV signal must also be within 1 micron of best focus so that the normal PDA measurements are not unduly sensitive to focus.

Another variable that can be used to adjust the focus curve is the position of aperture mirror 28. De-centering aperture mirror 28 laterally (vertically on the monitor image) will shift the position of the entire focus curve along the z-axis (the focus position axis). De-centering the aperture mirror should only be done while aligning the optics when other techniques are not sufficient. It should not be done during routine lamp changes. Usually the de-centering is necessary to compensate for some other effect in the system. If aperture mirror 28 is de-centered too much, the focus curve position is too sensitive to the aperture mirror position, and any small drift in alignment will shift the focus curve.

If the peaks of the individual UV and visible signals are at roughly the same z-position, it is usually fairly easy to adjust the focus curve. However, there are several factors that can separate the two "colors" (UV and visible) and cause them to peak at different z-positions. The largest effect, can be the image quality of the 15× objective lens (which is directly related to the wavefront distortion specification for this objective lens). Conventionally, it had been thought that an all-reflecting surface lens (such as the 15× objective employed in a preferred embodiment of the FIG. 2 system) should have absolutely no chromatic aberration; that is, all colors originating from the same point should be focused to the same "point" on the image. Actually, light can never be focused to a true point. It instead forms a diffraction pattern called the point spread function that usually has a central spike surrounded by dim concentric rings that decrease sharply in brightness away from the center. Shorter wavelength light will produce a more compact pattern. If a lens is achromatic, the point spread functions for each color are centered about the same point although they will have different diameters. In the FIG. 2 system, beam divider 45 only lets radiation through half of pupil stop 41 producing an oblong pattern stretched in one direction. If the objective lens quality is good, the point spread function will still be symmetric, and the centroids of all colors will still fall on top of each other. However, if the wavefront error of the objective is not good, the asymmetric illumination causes the point spread function to be asymmetric, and the centroids of the colors could be separated by a significant amount. When the UV and visible "colors" are separated laterally, they will peak at different z-positions as the radiation scans across the pinhole through plate 54 with focus.

A second effect that can separate the UV and visible "colors" is wavefront error caused by off-axis paraboloid mirror 16. If paraboloid mirror 16 is not well made, or if it is stressed by too much torque on its mounting screws, it can cause the same effect as a bad objective lens, although usually to a lesser degree.

A third effect is mainly determined by the illuminator design. Too much glass in the uncollimated parts of the optical path will cause true chromatic aberration, and the UV and visible "colors" will separate. For this reason, the lamp heatsink window is preferably very thin.

The described problems with the focus curve are usually encountered only while building the FIG. 2 system; not during normal operation or during lamp replacement. Adjusting the focus curve during a routine lamp change may be feasible for experienced operators. It is possible for a defect in the glass of the new lamp to distort the focus curve. With the FIG. 2 system, lamp noise is not usually a problem, but optimizing the focus curve may require significant time and skill.

The above-described autofocus subsystem of FIG. 2 (and FIG. 1) uses the image reflected from sample plate 54. Sample plate 54 is preferably a reflective fused silica plate with an aperture therethrough. For simplicity, an identical reflective fused silica plate with an aperture is used as reference plate 52, however reference plate 52 need not be reflecting.

The image reflected from sample plate 54 is also used for viewing wafer 3. As shown in FIG. 2, sample beam 46 is partially reflected off sample plate 54, through short focal length achromat 80, and reflects from mirror 89 into beamsplitter cube 84. Beamsplitter cube 84 splits the incoming beam into a camera beam 65 and a focus beam 63. Camera beam 65 is then reflected in penta prism 86, focused by long focal length achromat 90, filtered by N.D. filter 97, and reflected into video camera 96 by fold mirror 91. Penta prism 86 is used instead of a mirror, so that the image received by video camera 96 is a non-inverted image of wafer 3.

As shown in FIG. 2, long focal length achromat 88 directs beam 63 onto detector 98. In an alternative embodiment (not shown), where less space is available, long focal length achromat 88 is replaced by a medium focal length achromat and a negative lens such as a barlow lens. Turning mirrors are used if detector 98 is not mounted in the path of beam 63.

Beamsplitter cube 84 is positioned slightly off-axis so that unwanted reflections from the faces of beamsplitter cube 84 are skewed out of the optical path of the entering beam. This is accomplished by rotating the beamsplitter cube 1° to 10°, preferably 3° to 5°, about an axis normal to the reflection surface within the cube. Similarly, penta prism 86 is rotated in the plane of reflection to remove unwanted reflections from the field of view. Additionally, to capture stray radiation from unwanted internal reflections within beamsplitter cube 84, black glass is glued to the unused surfaces of beamsplitter cube 84. In this way, only the desired internal reflection of beam 65 and beam 63 exit beamsplitter cube 84.

An embodiment and variations of an optical system according to the present invention has been described. That description is illustrative and not restrictive. Many variations of the invention will become apparent to those of skill in the art upon review of this disclosure. Merely by way of example, the z-position of a sample portion (where the x and y-positions of the sample have changed) could be estimated from a known sample tilt; the sample measured by the invention need not be a wafer, but can be any other reflective object; and fold mirrors can be removed where space allows, and additional fold mirrors can be provided where space is limited. The scope of the invention should be determined not merely with reference to the above description, but should be determined with reference to the appended claims along with their full scope of equivalents.

What is claimed is:

1. A method for performing optical reflectance measurements on a sample having a very thin film, the method including the steps of:

(a) focusing a first beam of radiation onto a selected area of the sample, said first beam including UV components in a UV frequency band and visible components in a visible frequency band;

(b) receiving a reflected portion of the first beam that has reflected from the selected area, and separating the reflected portion into a second beam including the UV components and a third beam including the visible components;

(c) generating a first signal indicative of intensity of the second beam;

(d) generating a second signal indicative of intensity of the third beam;

(e) processing the first signal and the second signal to generate a reflected ratio signal indicative of relative intensity of the second beam and the third beam; and (f) processing the reflected ratio signal to generate data indicative of thickness of the very thin film.

2. The method of claim 1, wherein step (f) includes the steps of:

correcting the reflected ratio signal to generate a reflectance ratio signal indicative of sample reflectance in the UV frequency band divided by sample reflectance in the visible frequency band; and processing the reflectance ratio signal to generate said data indicative of thickness of the very thin film.

3. The method of claim 2, wherein the reflected ratio signal has a value, ISAMP, substantially equal to intensity of the second beam divided by intensity of the third beam, said method also including the steps of:

focusing the first beam onto a reference sample and separating reflected radiation from the reference sample into a fourth beam including UV components reflected from the reference sample and a fifth beam including visible components reflected from the reference sample;

generating a fourth signal indicative of intensity of the fifth beam;

focusing the first beam onto a calibration sample and separating reflected radiation from the calibration sample into a sixth beam including UV components reflected from the reference sample and a seventh beam including visible components reflected from the calibration sample;

generating a fifth signal indicative of intensity of the seventh beam; and wherein the reflectance ratio signal has a value substantially equal to $$R = (ISAMP/ICHIP2)(ICHIP1/ICAL)(RCALUV/RCALVIS),$$

where ICHIP2 represents intensity of the second beam divided by intensity of the fifth beam just prior to generation of the first signal, ICHIP1 represents intensity of the second beam divided by intensity of the fifth beam during a reflectance calibration, ICAL represents intensity of the second beam divided by intensity of the seventh beam, RCALUV represents reflectance of the calibration sample at an effective UV wavelength, and RCALVIS represents reflectance of the calibration sample at an effective visible wavelength.

4. The method of claim 3, wherein each of the values ISAMP, ICHIP2, ICHIP1, and ICAL, represents intensity with a darknoise DC level subtracted therefrom.

5. The method of claim 1, wherein step (f) includes the step of:

determining a first effective wavelength of the second beam and a second effective wavelength of the third beam.

6. The method of claim 5, wherein the step of determining the first effective wavelength and the second effective wavelength includes the steps of:

generating a first measured value ($I1_u$) indicative of intensity of UV components reflected from a first calibration wafer, a second measured value ($I1_v$) indicative of intensity of visible components reflected from the first calibration wafer, a third measured value ($I2_u$) indicative of intensity of UV components reflected from a second calibration wafer, a fourth measured value ($I2_v$) indicative of intensity of visible components reflected from the second calibration wafer, a fifth measured value ($I3_u$) indicative of intensity of UV components reflected from a third calibration wafer, a sixth measured value ($I3_v$) indicative of intensity of visible components reflected from the third calibration wafer, a seventh measured value (ICHIP1') indicative of intensity of UV components reflected from a reference sample just prior to measuring the first measured value, an eighth measured value (ICHIP2') indicative of intensity of visible components reflected from the reference sample just prior to measuring the first measured value, a ninth measured value (ICHIP3') indicative of intensity of UV components reflected from the reference sample just prior to measuring the third measured value, a tenth measured value (ICHIP4') indicative of intensity of visible components reflected from the reference sample just prior to measuring the third measured value, an eleventh measured value (ICHIP5') indicative of intensity of UV components reflected from the reference sample just prior to measuring the fifth measured value, and a twelfth measured value (ICHIP6') indicative of intensity of visible components reflected from the reference sample just prior to measuring the fifth measured value, wherein each of the first calibration wafer, the second calibration wafer, and the third calibration wafer has a thin film of known thickness;

generating a first ratio signal indicative of the value ($I1_u/I1_v$)/(ICHIP1'/ICHIP2');

generating a second ratio signal indicative of the value ($I2_u/I2_v$)/(ICHIP3'/ICHIP4');

generating a third ratio signal indicative of the value ($I3_u/I3_v$)/(ICHIP5'/ICHIP6'); and processing the first ratio signal, the second ratio signal, and the third ratio signal to determine the first effective wavelength and the second effective wavelength.

7. The method of claim 6, wherein each of the values $I1_u$, $I1_v$, ICHIP1', ICHIP2', $I2_u$, $I2_v$, ICHIP3', ICHIP4', $I3_u$, $I3_v$, ICHIP5', and ICHIP6' represents intensity with a darknoise DC level subtracted therefrom.

8. The method of claim 1, wherein the second beam has an effective wavelength in a range from 350 to 370 nanometers, and the third beam has an effective wavelength in a range from 500 to 550 nanometers.

9. The method of claim 1, also including the steps of:

generating an illuminating beam and separating said illuminating beam into the first beam and a reference beam;

receiving a reflected portion of the reference beam that has reflected from a reference mirror, and separating the reflected portion of the reference beam into a fourth beam including UV components and a fifth beam including visible components;

generating a third signal indicative of intensity of the fourth beam;

generating a fourth signal indicative of intensity of the fifth beam, and wherein step (f) includes the step of processing the reflected ratio signal, the third signal, and the fourth signal to generate said data indicative of thickness of the very thin film.

10. A system for performing optical reflectance measurements on a sample, said system including:

a radiation source for emitting a first beam of radiation having UV components in a UV frequency band and visible components in a visible frequency band;

focusing means for focusing a portion of the first beam onto a selected area of the sample;

color separation means for receiving a reflected portion of the first beam that has reflected from the selected area, and separating the reflected portion into a second beam including the UV components and a third beam including the visible components;

first detector means for receiving the second beam and generating a first signal indicative of intensity of the second beam;

second detector means for receiving the third beam and generating a second signal indicative of intensity of the third beam; and processing means for generating a reflected ratio signal indicative of relative intensity of the second beam and the third beam, by processing the first signal and the second signal.

11. The system of claim 10, wherein the processing means is programmed with software for correcting the reflected ratio signal to generate a reflectance ratio signal indicative of sample reflectance in the UV frequency band divided by sample reflectance in the visible frequency band.

12. The system of claim 11, wherein the sample includes a very thin film, and wherein the processing means is also programmed with software for processing the reflectance ratio signal to generate data indicative of thickness of the very thin film.

13. The system of claim 12, wherein the processing means is programmed with software for determining a first effective wavelength of the second beam and a second effective wavelength of the third beam.

14. The system of claim 11, wherein the reflected ratio signal has a value substantially equal to ISAMP=intensity of the second beam divided by intensity of the third beam, wherein the focusing means is capable of focusing a portion of the first beam onto a reference sample and a calibration sample, the color separation means is capable of receiving reflected radiation from the reference sample and from the calibration sample, separating the reflected radiation from the reference sample into a fourth beam including UV components reflected from the reference sample and a fifth beam including visible components reflected from the reference sample, and separating the reflected radiation from the calibration sample into a sixth beam including UV components reflected from the calibration sample and a seventh beam including visible components reflected from the calibration sample, the second detector means receives the fifth beam and generates a fourth signal indicative of intensity of the fifth beam, and the second detector means receives the seventh beam and generates a fifth signal indicative of intensity of said seventh beam, and wherein the reflectance signal ratio has value substantially equal to

R=(ISAMP/ICHIP2)(ICHIP1/ICAL)(RCALUV/RCALVIS), where ICHIP2 represents intensity of the second beam divided by intensity of the fifth beam just prior to generation of the first signal, ICHIP1 represents intensity of the second beam divided by intensity of the fifth beam during a reflectance calibration, ICAL represents intensity of the second beam divided by intensity of the seventh beam, RCALUV represents reflectance of the calibration sample at an effective UV wavelength, and RCALVIS represents reflectance of the calibration sample at an effective visible wavelength.

15. The system of claim 14, wherein each of the values ISAMP, ICHIP2, ICHIP1, and ICAL, represents intensity with a darknoise DC level subtracted therefrom.

16. The system of claim 10, wherein the color separation means also includes:
   a first filter which receives the second beam and transmits only components of said second beam having wavelength in a first range of width from about 120 to about 200 nanometers to the first detector means; and
   a second filter which receives the third beam and transmits only components of said third beam having wavelength in a second range of width from about 120 to about 200 nanometers to the second detector means.

17. The system of claim 16, wherein the first range is from about 280 to 400 nanometers and the second range is from about 400 to 600 nanometers.

18. The system of claim 16, wherein the processing means generates a first effective wavelength of the second beam and a second effective wavelength of the third beam.

19. The system of claim 18, wherein the first effective wavelength is in a range from 350 to 370 nanometers, and the second effective wavelength is in a range from 500 to 550 nanometers.

20. The system of claim 10, wherein the color separation means includes a dichroic element for receiving said reflected portion of the first beam, and transmitting a third portion of said reflected portion of the first beam, the system also including:
   a diffraction grating for receiving and diffracting the third portion; and
   a sample channel photodiode array for receiving the diffracted third portion from the diffraction grating.

21. The system of claim 20, also including:
   a baffle between the diffraction grating and at least one of the first detector means and the second detector means, for preventing diffracted radiation from the diffraction grating from reaching said at least one of the first detector means and the second detector means.

22. The system of claim 21, wherein the color separation means includes a dichroic mirror with a front face and a back face, the front face is highly reflective to components of the reflected portion of the first beam having wavelength from 280 nm to 400 nm and highly transmissive to components of the reflected portion of the first beam having wavelength above 400 nm, the back face has a metallic coating, and the metallic coating is partially reflective to those components of the reflected portion of the first beam having wavelength above 400 nm which are transmitted through the front face.

23. The system of claim 22, also including:
   a UV filter between the dichroic mirror and the first detector means, for removing residual visible light reflected from the front face of the dichroic mirror; and
   a second filter between the dichroic mirror and the second detector means, for transmitting to the second detector means only components, of the reflected portion of the first beam which are reflected from the metallic coating, in a band of wavelengths centered near 500 nm.

24. The system of claim 23, wherein the band of wavelengths is not more than about 200 nm wide.

25. The system of claim 23, wherein the UV filter is a color glass filter which blocks substantially all light between 400 nm and 700 nm, and the second filter includes two color glass filters bonded together.

26. The system of claim 23, wherein the metallic coating reflects X % of the components of the reflected portion of the first beam having wavelength above 400 nm which are transmitted through the front face, where X % is substantially equal to 40%.

27. The system of claim 10, also including:
   a beamsplitter which diverts a sample portion of the first beam from the radiation source to the focusing means, and wherein said focusing means includes:
   an objective lens; and
   a pupil stop member positioned between the beamsplitter and the objective lens, wherein a first aperture extends through the pupil stop member and a second aperture smaller than the first aperture extends through the pupil stop member, and wherein the pupil stop member is oriented relative to the beamsplitter so that a portion of the sample beam having substantially uniform cross-section passes through the first aperture before reaching the selected area, and a reflected subportion of said portion of the sample beam passes through the second aperture after said portion of the sample beam has reflected from the selected area.

28. The system of claim 27, wherein a third aperture extends through the pupil stop member and a fourth aperture extends through the pupil stop member, wherein the third aperture and the first aperture have substantially equal areas and the fourth aperture is substantially smaller than the first aperture, and wherein the pupil stop member is oriented relative to the beamsplitter so that portions of the sample beam having substantially uniform cross-section pass through both the first aperture and the third aperture before reaching the selected area, and reflected subportions of said portions of the sample beam pass through the second aperture and the fourth aperture after said portion of the sample beam has reflected from the selected area.

29. The system of claim 10, wherein at least one of the focusing means and the color separation means includes:
   means for reducing sensitivity, of the intensity of the second beam and the intensity of the third beam, to tilt of the sample relative to the focusing means.

30. The system of claim 29, also including:
   a beamsplitter which diverts a sample portion of the first beam from the radiation source to the focusing means, and wherein said means for reducing sensitivity includes:
   an objective lens in the focusing means; and
   a pupil stop member positioned in the focusing means between the beamsplitter and the objective lens, wherein a first aperture extends through the pupil stop member and a second aperture smaller than the first aperture extends through the pupil stop member, and wherein the pupil stop member is oriented relative to the beamsplitter so that a portion of the sample beam having substantially uniform cross-section passes through the first aperture before reaching the selected area, and a reflected subportion of said portion of the sample beam passes through the second aperture after said portion of the sample beam has reflected from the selected area.

31. A system for performing optical reflectance measurements on a sample, said system including:
   a radiation source for emitting a first beam of radiation;
   an objective lens;

a beamsplitter for diverting a sample beam of said radiation from the radiation source toward the objective lens and directing a reference beam portion of the first beam away from the objective lens;

a pupil stop member positioned between the beamsplitter and the objective lens, wherein a first aperture extends through the pupil stop member and a second aperture smaller than the first aperture extends through the pupil stop member, and wherein the pupil stop member is oriented relative to the beamsplitter so that a portion of the sample beam having substantially uniform cross-section passes through the first aperture and is then focused by the objective lens onto a selected area of the sample, and a reflected portion of said sample beam passes through the second aperture after reflecting from the selected area and is then transmitted through the beamsplitter; and a detector assembly positioned for receiving at least a portion of said reflected portion of the sample beam that has transmitted through the beamsplitter.

32. The system of claim 31, wherein a third aperture extends through the pupil stop member and a fourth aperture extends through the pupil stop member, wherein the third aperture and the first aperture have substantially equal areas and the fourth aperture is substantially smaller than the first aperture, and wherein the pupil stop member is oriented relative to the beamsplitter so that portions of the sample beam having substantially uniform cross-section pass through both the first aperture and the third aperture before reaching the selected area, and reflected subportions of said portions of the sample beam pass through the second aperture and the fourth aperture after said portion of the sample beam has reflected from the selected area.

33. The system of claim 31, wherein the detector assembly includes:

a color separation means for receiving said portion of said reflected portion of the sample beam that has reflected from the selected area, and separating said reflected portion into a second beam including UV components and a third beam including visible components;

first detector means for receiving the second beam and generating a first signal indicative of intensity of the second beam; and second detector means for receiving the third beam and generating a second signal indicative of intensity of the third beam.

34. The system of claim 33, wherein the first detector means is a photodiode and the second detector means is another photodiode.

35. The system of claim 33, also including:

processing means for generating a reflected ratio signal indicative of relative intensity of the second beam and the third beam, by processing the first signal and the second signal.

36. The system of claim 33, wherein the color separation means includes a dichroic element for receiving said reflected portion of the sample beam, and transmitting a third portion of said reflected portion of the sample beam, and wherein the detector assembly also includes:

a diffraction grating for receiving and diffracting the third portion; and a sample channel photodiode array for receiving the diffracted third portion from the diffraction grating.

37. The system of claim 36, also including a baffle between the diffraction grating and at least one of the first detector means and the second detector means, for preventing diffracted radiation from the diffraction grating from reaching said at least one of the first detector means and the second detector means.

38. A method for performing optical reflectance measurements on a sample having a very thin film, the method including the steps of:

(a) generating a first beam of radiation including UV components in a UV frequency band, and dividing the first beam into a sample beam and a reference beam;

(b) focusing the sample beam onto a selected area of the sample;

(c) receiving a reflected portion of the sample beam that has reflected from the selected area and generating a first signal indicative of intensity of said reflected portion of the sample beam;

(d) receiving a reflected portion of the reference beam that has reflected from a reference mirror and generating a second signal indicative of intensity of said reflected portion of the reference beam;

(e) processing the first signal and the second signal to generate a reflectance signal indicative of reflectance of the sample;

(f) processing the reflectance signal to generate data indicative of thickness of the very thin film, wherein step (f) includes the step of determining an effective wavelength of the first signal, by:

generating a first measured value (I1) indicative of intensity of the first beam reflected from a first calibration wafer, a second measured value (I2) indicative of intensity of the first beam reflected from a second calibration wafer, a third measured value (ICHIP1') indicative of intensity of the first beam reflected from a reference sample just prior to measuring the first measured value, a fourth measured value (ICHIP2') indicative of intensity of the first beam reflected from the reference sample just prior to measuring the second measured value;

generating a first ratio signal indicative of the value (I1/(ICHIP1'));

generating a second ratio signal indicative of the value (I2/(ICHIP2')); and processing the first ratio signal and the second ratio signal to determine the first effective wavelength.

39. The method of claim 38, wherein each of the values I1, I2, ICHIP1', and ICHIP2' represents intensity of the sample beam with a darknoise DC level subtracted therefrom, divided by intensity of the reference beam with said darknoise DC level subtracted therefrom.

40. The method of claim 38, wherein each of the values I1, I2, ICHIP1', and ICHIP2' represents intensity of the sample beam divided by intensity of the reference beam.

41. The method of claim 40, wherein step (e) includes the steps of:

focusing the sample beam onto a reference sample, and receiving a reflected portion of the sample beam that has reflected from the reference sample and generating a third signal indicative of intensity of said reflected portion of the sample beam; and focusing the sample beam onto a calibration sample, and receiving a reflected portion of the sample beam that has reflected from the calibration sample and generating a fourth signal indicative of intensity of said reflected portion of the sample beam; and wherein the reflectance signal has a value substantially equal to

R=(ISAMP/ICHIP2)(ICHIP1/ICAL)(RCAL), where ISAMP represents intensity of the first signal divided by intensity of the second signal, ICHIP2 represents intensity of the third signal divided by intensity of the second signal just prior to generation of the first signal, ICHIP 1 represents intensity of the third signal divided by intensity of the second signal during a reflectance calibration, ICAL represents intensity of the fourth signal divided by intensity of the second signal during another reflectance calibration, and RCAL represents reflectance of the calibration sample at the first effective wavelength.

42. The method of claim 41, wherein each of the values ISAMP, ICHIP2, ICHIP1, and ICAL, represents intensity with a darknoise DC level subtracted therefrom divided by intensity of the second signal with the darknoise DC level subtracted therefrom.

\* \* \* \* \*